US007767701B2

(12) United States Patent
Hasegawa et al.

(10) Patent No.: US 7,767,701 B2
(45) Date of Patent: Aug. 3, 2010

(54) CHEMICAL COMPOUNDS

(75) Inventors: Masaichi Hasegawa, Ibaraki (JP); Jun Tang, Ibaraki (JP); Hideyuki Sato, Ibaraki (JP)

(73) Assignee: GlaxoSmithKline LLC, Philadelphia, PA (US)

( * ) Notice: Subject to any disclaimer, the term of this patent is extended or adjusted under 35 U.S.C. 154(b) by 863 days.

(21) Appl. No.: 10/535,690

(22) PCT Filed: Nov. 18, 2003

(86) PCT No.: PCT/US03/37658

§ 371 (c)(1),
(2), (4) Date: Apr. 10, 2006

(87) PCT Pub. No.: WO2004/047760

PCT Pub. Date: Jun. 10, 2004

(65) Prior Publication Data

US 2006/0293338 A1   Dec. 28, 2006

Related U.S. Application Data

(60) Provisional application No. 60/428,384, filed on Nov. 22, 2002.

(51) Int. Cl.
*C07D 417/08* (2006.01)
*C07D 417/10* (2006.01)
*C07D 417/12* (2006.01)
*C07D 417/14* (2006.01)
*A61K 31/47* (2006.01)
*A61K 31/4427* (2006.01)
*A61K 31/42* (2006.01)
*A61K 31/435* (2006.01)
*A61P 7/04* (2006.01)
*A61P 7/06* (2006.01)

(52) U.S. Cl. ............. 514/369; 548/184; 548/146; 548/217; 548/311.1; 546/152; 546/184; 546/268.1; 546/279.1; 546/112; 544/359; 544/353; 514/249; 514/252.13; 514/317; 514/311; 514/336; 514/359; 514/366; 514/372

(58) Field of Classification Search ............. 548/184; 514/369
See application file for complete search history.

(56) References Cited

U.S. PATENT DOCUMENTS

| 3,678,041 | A | 7/1972 | Mousseron |
| 3,704,296 | A | 11/1972 | Mousseron |
| 5,143,928 | A | 9/1992 | Cetenko et al. |
| 5,145,753 | A | 9/1992 | Irino et al. |
| 5,290,800 | A | 3/1994 | Cetenko et al. |
| 5,306,822 | A | 4/1994 | Cetenko et al. |
| 5,374,652 | A | 12/1994 | Buzzetti et al. |
| 5,494,927 | A | 2/1996 | Cetenko et al. |
| 5,523,314 | A | 6/1996 | Bue-Valleskey et al. |
| 5,554,767 | A | 9/1996 | Wang et al. |
| 5,618,835 | A | 4/1997 | Wu et al. |
| 5,843,970 | A | 12/1998 | Pershadsingh et al. |
| 5,958,957 | A | 9/1999 | Anderson et al. |
| 6,011,031 | A | 1/2000 | Lohray et al. |
| 6,221,613 | B1 | 4/2001 | Salon et al. |
| 6,410,734 | B1 | 6/2002 | Hu et al. |
| 6,583,140 | B2 | 6/2003 | Hu et al. |
| 6,685,767 | B2 | 2/2004 | Noro et al. |
| 6,689,491 | B1 | 2/2004 | Nii et al. |
| 2002/0155381 | A1 | 10/2002 | Berneth et al. |
| 2004/0097566 | A1 | 5/2004 | Pfal et al. |

FOREIGN PATENT DOCUMENTS

| DE | 270072 A1 | 7/1989 |
| EP | 0304493 B1 | 9/1988 |
| EP | 554834 A2 | 11/1993 |
| EP | 587229 | 3/1994 |
| EP | 587230 | 3/1994 |
| EP | 587377 | 3/1994 |
| EP | 677517 | 10/1995 |
| EP | 697410 A1 | 2/1996 |
| JP | 55045648 | 3/1980 |
| JP | 01097926 | 4/1989 |
| JP | 05002200 A2 | 1/1993 |
| JP | 05333468 | 12/1993 |
| JP | 06128234 | 5/1994 |
| JP | 08109176 | 4/1996 |
| JP | 09255669 A | 9/1997 |
| JP | 3155050 | 2/2001 |
| JP | 2001348520 A | 12/2001 |
| WO | WO 96/26207 | 8/1996 |
| WO | WO 98/37073 | 8/1998 |
| WO | WO 99/59586 | 11/1999 |
| WO | WO00/18748 | 4/2000 |

(Continued)

OTHER PUBLICATIONS

Mass, R. D., Int. J. Radiation Oncology Bio. Phys.vol. 58(3): 932-940, 2004.*

(Continued)

*Primary Examiner*—Venkataraman Balasubramanian
(74) *Attorney, Agent, or Firm*—Wayne J. Dustman; Edward J. Gimmi

(57) ABSTRACT

This invention relates to newly identified compounds for inhibiting hYAK3 proteins and methods for treating diseases associated with the imbalance or inappropriate activity of hYAK3 proteins.

6 Claims, No Drawings

FOREIGN PATENT DOCUMENTS

| WO | WO 01/02394 | 1/2001 |
|---|---|---|
| WO | WO 02/06245 | 1/2002 |
| WO | WO 02/051409 | 7/2002 |
| WO | WO 03/050098 | 6/2003 |

OTHER PUBLICATIONS

Fabbro et al. Pharmacology & therapeutics 93, 79-98, 2002.*
Cecil Textbook of Medicine, edited by Bennet, J.C., and Plum F., 20th edition, vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Fahmy, H.M., J. Chem. Soc., 1985, Perkins Trans. 2, 1, pp. 45-49.
Johnson, et al., Biochemistry, 2001, vol. 40, pp. 7736-7745.
Phillips A.P., J. Am. Chem. Soc., 1945, vol. 67, pp. 744-748.
Gupta, et al., J. Indian Chem. Soc., 1978, vol. 55, No. 5, pp. 483-485.
Gershuns, et al., Ukrain, Khim. Zhur., 1959, vol. 25, pp. 639-643. (translated).
Burton, et al., J. Med. Chem., 1970, vol. 13, No. 5, pp. 1009-1011.
J. Pharm. Sci., 1977, vol. 66, pp. 1607-1611.
Akerblom, J. Med. Chem., 1974, vol. 17, pp. 609-615.
Sugasawa, et al., Pharm. Bull., 1953, vol. 1, pp. 281-282.
Walker, J. Chem. Research, Synopses (11), 1913, vol. 460, pp. 1127-1143.
Shikhaliev, Khimicheskaya Tekhnologiya, 2000, vol. 43, No. 2, pp. 95-98. (translated).
Raouf, et al., Acta Chim. Acad. Sci. Hung., 1975, vol. 87, No. 2, pp. 187-193.
Raouf, et al., Acta Chim. Acad. Sci. Hung., 1974, vol. 83, No. 3-4, pp. 359-365.
Harhash, et al., Egypt J. Chem., 1972, vol. 15, No. 1, pp. 11-21.
Pailer, et al., Monatsh. Chem., 1958, vol. 89, pp. 175 and 185. (translated).
Behringer, e tal., Chem. Ber, 1958, vol. 91, 2773 and 2783 or 2773-2783. (translated).
Gilbert, et al., J. Chem. Soc., 1954, pp. 3919-3921.
Brown, et al., J. Chem Soc., 1952, pp. 4397-4400.
Julian, et al., Amer. Chem. Soc., 1935, vol. 57, pp. 1126-1128.
Atti Accad. Naz. Lincei Cl. Sci. Fis. Mat. Nat. Rend., 1906, vol. 15 I, pp. 42. (translated).
Gazz. Chi. Ital., 1906, vol. 36 II, pp. 140. (translated).
Andreasch, et al., Monatsh. Chem., 1904, vol. 25, pp. 159-174. (translated).
Andreasch, et al., Monatsh. Chem., 1903, vol. 24, pp. 505-506.
Abdel-Halim, Indian J. of Heterocyclic Chem., 1994, vol. 4, No. 1, pp. 45-50.
Chadha, et al., Indian J. Chem., 1971, vol. 9, No. 9, pp. 910-912.
Bhargava, et al., J. Indian Chem. Soc., 1958, vol. 35, pp. 161-164.
Stieger, Monatsh Chem., 1916, vol. 37, pp. 651. (translated).
Mandlik, et al., J. Univ. Poona, Sci. Technol., 1966, No. 32, pp. 43-46.
Khodair, et al., J. of Heterocyclic Chem., 2002, vol. 39, No. 6, pp. 1153-1160.
Izvestiya Vysshikh Uchebnykh Zavedenii, Khimiya I Khimicheskaya Tekhnologiya, 1979, vol. 22, No. 12, pp. 1445-1448.
Chaudhary, et al., Indian J. of Chem., 1968, vol. 6, No. 9, pp. 488-489.
Mandlik, et al., J. Univ. Poona. Sci. Technol., 1961, vol. No. 1, 20, pp. 41-43.
Shah, et al., J. Indian Chem. Soc., 1959, vol. 36, pp. 731-732.
Das, et al., J. of Scientific & Industrial Research, 1957, vol. 16C, pp. 125-126.
Tyle, et al., Pharmaceutical Research, vol. 3, No. 6, 1986, pp. 318-326.
Lord, et al., Blood, 2000, vol. 95, No. 9. pp. 2838-2846.
Serrano, et al., Nature, 1993, vol. 366, pp. 704-707.
Raap, et al., Eur. J. Org. Chem., 1999, pp. 2609-2621.
Kamb, et al., Science, 1994, vol. 264, pp. 436-440.
Peter & Herskowitz, Cell, 1994, vol. 79, pp. 181-184.
Plobeck, et al., J. Med. Chem., 2000, vol. 43, pp. 3878-3894.
Kunishima, et al., J. Am. Chem. Soc., 1999, vol. 121, pp. 4722-4723.
Garrett, et al., Mol. Cell. Biol., 1991, vol. 11, pp. 4045-4052.

* cited by examiner

CHEMICAL COMPOUNDS

This application claims the benefit of U.S. Provisional Application No. 60/428,384 filed Nov. 22, 2002.

FIELD OF THE INVENTION

This invention relates to newly identified compounds for inhibiting hYAK3 proteins and methods for treating diseases associated with the imbalance or inappropriate activity of hYAK3 proteins.

BACKGROUND OF THE INVENTION

A number of polypeptide growth factors and hormones mediate their cellular effects through a signal transduction pathway. Transduction of signals from the cell surface receptors for these ligands to intracellular effectors frequently involves phosphorylation or dephosphorylation of specific protein substrates by regulatory protein serine/threonine kinases (PSTK) and phosphatases. Serine/threonine phosphorylation is a major mediator of signal transduction in multicellular organisms. Receptor-bound, membrane-bound and intracellular PSTKs regulate cell proliferation, cell differentiation and signalling processes in many cell types.

Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are potential targets for drug design.

A subset of PSTKs are involved in regulation of cell cycling. These are the cyclin-dependent kinases or CDKs (Peter and Herskowitz, Cell 1994: 79, 181-184). CDKs are activated by binding to regulatory proteins called cyclins and control passage of the cell through specific cell cycle checkpoints. For example, CDK2 complexed with cyclin E allows cells to progress through the G1 to S phase transition. The complexes of CDKs and cyclins are subject to inhibition by low molecular weight proteins such as p16 (Serrano et al, Nature 1993: 366, 704), which binds to and inhibits CDK4. Deletions or mutations in p16 have been implicated in a variety of tumors (Kamb et al, Science 1994: 264, 436440). Therefore, the proliferative state of cells and diseases associated with this state are dependent on the activity of CDKs and their associated regulatory molecules. In diseases such as cancer where inhibition of proliferation is desired, compounds that inhibit CDKs may be useful therapeutic agents. Conversely, activators of CDKs may be useful where enhancement of proliferation is needed, such as in the treatment of immunodeficiency.

YAK1, a PSTK with sequence homology to CDKs, was originally identified in yeast as a mediator of cell cycle arrest caused by inactivation of the cAMP-dependent protein kinase PKA (Garrett et al, Mol Cell Biol. 1991: 11-60454052). YAK1 kinase activity is low in cycling yeast but increases dramatically when the cells are arrested prior to the S-G2 transition. Increased expression of YAK1 causes growth arrest in yeast cells deficient in PKA. Therefore, YAK1 can act as a cell cycle suppressor in yeast.

Our U.S. Pat. No. 6,323,318 describes two novel human homologs of yeast YAK1 termed hYAK3-2, one protein longer than the other by 20 amino acids. hYAK3-2 proteins (otherwise reported as REDK-L and REDK-S in *Blood,* 1 May 2000, Vol 95, No. 9, pp2838) are primarily localized in the nucleus. hYAK-2 proteins (hereinafter simply referred as hYAK3 or hYAK3 proteins) are present in hematopoietic tissues, such as bone marrow and fetal liver, but the RNA is expressed at significant levels only in erythroid or erthropoietin (EPO)-responsive cells. Two forms of REDK cDNAs appear to be alternative splice products. Antisense REDK oligonucleotides promote erythroid colony formation by human bone marrow cells, without affecting colony-forming unit (CFU)-GM, CFU-G, or CFU-GEMM numbers. Maximal numbers of CFU-E and burst-forming unit-erythroid were increased, and CFU-E displayed increased sensitivity to suboptimal EPO concentrations. The data indicate that REDK acts as a brake to retard erythropoiesis. Thus inhibitors of hYAK3 proteins are expected to stimulate proliferation of cells in which it is expressed. More particularly, inhibitors of hYAK3 proteins are useful to treat or prevent diseases of the erythroid and hematopoietic systems mediated the imbalance or inappropriate activity of hYAK3 proteins, including but not limited to, anemias due to renal insufficiency or to chronic disease, such as autoimmunity, HIV, or cancer, and drug-induced anemias, myelodysplastic syndrome, aplastic anemia and myelosuppression, and cytopenia.

SUMMARY OF THE INVENTION

In a first aspect, the instant invention relates a method of inhibiting hYAK3 in a mammal; comprising, administering to the mammal a therapeutically effective amount of a compound of the formula I, or a salt, solvate, or a physiologically functional derivative thereof

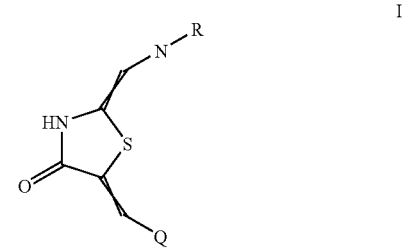

in which
R is $C_{3-6}$ cycloalkyl or naphtyl; or
R is

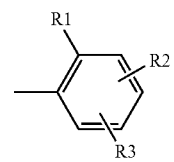

in which R1 is hydrogen, halogen, —$C_{1-6}$alkyl, —$SC_{1-6}$alkyl, —$OC_{1-6}$alkyl, —$NO_2$,
—S(=O)—$C_{1-6}$alkyl, —OH, —$CF_3$, —CN, —$CO_2$H, —$OCF_3$, or —$CO_2C_{1-6}$alkyl;
and R2 and R3 are independently hydrogen, halogen, —$C_{1-6}$ alkyl, —$SC_{1-6}$alkyl, —$OC_{1-6}$alkyl, —$NO_2$, —S(=O)—$C_{1-6}$alkyl, —OH, —$CF_3$, —CN, —$CO_2$H, —$CO_2C_{1-6}$alkyl, —$CONH_2$, —$NH_2$, —$OCH_2$(C=O) OH, —$OCH_2CH_2OCH_3$, —$SO_2NH_2$,
—$CH_2SO_2CH_3$, —NH(C=NH)$CH_3$; or R2 and R3 can independently be a radical of the formula R is

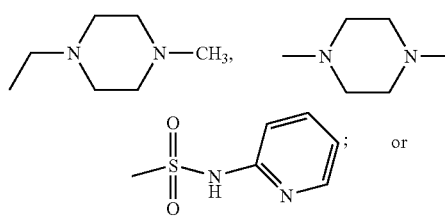

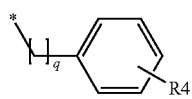

in which q is one or two; R4 is hydrogen, halogen, or —SO$_2$NH$_2$; or

R is —(CH$_2$)$_n$—NR$^k$R$^l$ in which n is 2 or 3, and R$^k$ and R$^l$ are independently —C$_{1-6}$alkyl; or —NR$^k$R$^l$ together form

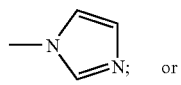

R is

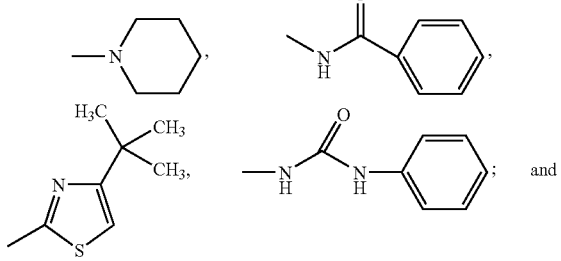

Q is

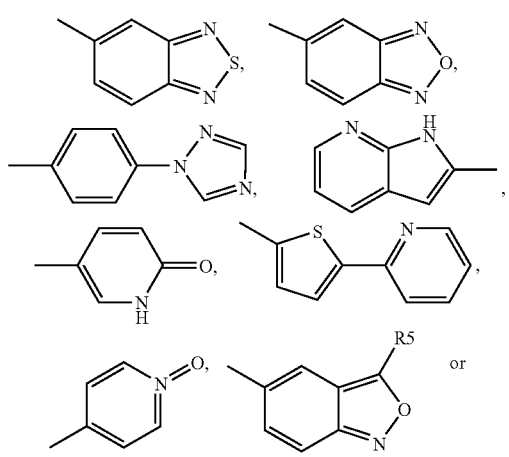

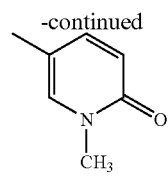

in which R5 is hydrogen, phenyl optionally substituted with up to three C$_{1-6}$ alkyl or halogen, or C$_{1-6}$ alkyl; or Q is

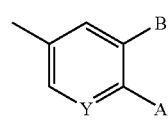

in which Y is CH; and A and B together are a part of

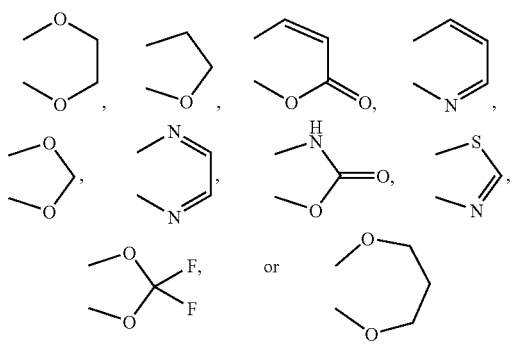

provided that ortho position to Y is N or O; or

Q is

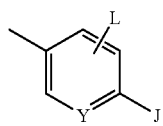

in which Y is N or CH; J is hydrogen, NH$_2$, OH or —OC$_{1-6}$ alkyl; and L is hydrogen, NH$_2$, halogen, —NO$_2$, or —OC$_{1-6}$alkyl.

In a second aspect of the present invention, there is provided a compound of the formula II, or a salt, solvate, or a physiologically functional derivative thereof

I

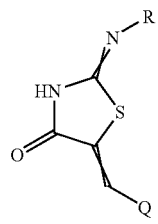

in which

R is $C_{3-6}$ cycloalkyl or naphtyl; or

R is

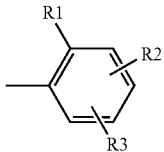

in which R1 is hydrogen, halogen, —$C_{1-6}$alkyl, —$SC_{1-6}$alkyl, —$OC_{1-6}$alkyl, —$NO_2$,
—S(=O)—$C_{1-6}$alkyl, —OH, —$CF_3$, —CN, —$CO_2H$, —$OCF_3$, or —$CO_2C_{1-6}$alkyl;

and R2 and R3 are independently hydrogen, halogen, —$C_{1-6}$ alkyl, —$SC_{1-6}$alkyl, —$OC_{1-6}$alkyl, —$NO_2$, —S(=O)—$C_{1-6}$alkyl, —OH, —$CF_3$, —CN, —$CO_2H$, —$CO_2C_{1-6}$alkyl, —$CONH_2$, —$NH_2$, —$OCH_2(C=O)OH$, —$OCH_2CH_2OCH_3$, —$SO_2NH_2$, —$CH_2SO_2CH_3$, —NH(C=NH)$CH_3$; or R2 and R3 can independently be a radical of the formula

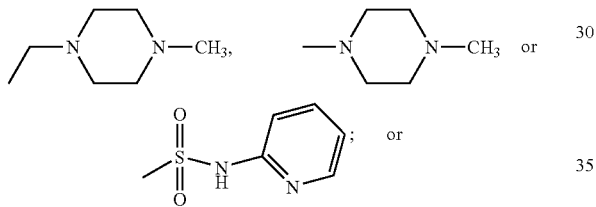

R is

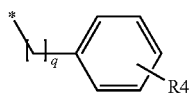

in which q is one or two; R4 is hydrogen, halogen, or —$SO_2NH_2$; or

R is —$(CH_2)_n$—$NR^kR^l$ in which n is 2 or 3, and $R^k$ and $R^l$ are independently —$C_{1-6}$alkyl; or —$NR^kR^l$ together form

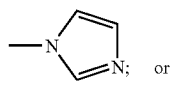

R is

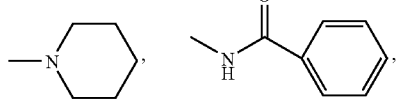

-continued

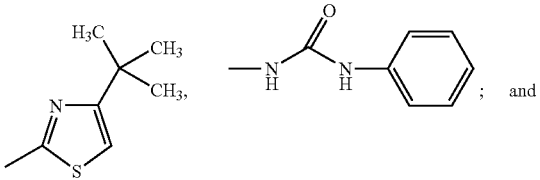

Q is

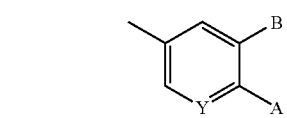

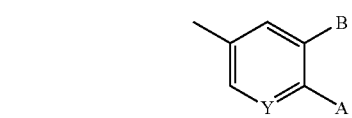

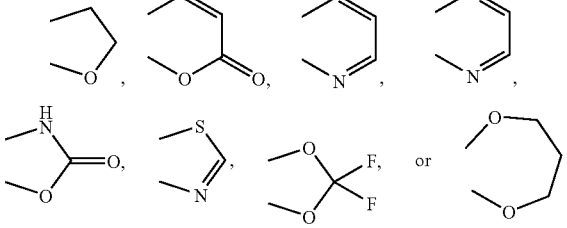

in which R5 is hydrogen, phenyl optionally substituted with up to three $C_{1-6}$ alkyl or halogen, or $C_{1-6}$ alkyl; or Q is

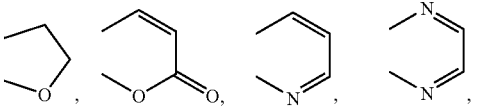

in which Y is CH; and A and B together are a part of provided that ortho position to Y is N or O.

In one embodiment, in a compound of formula I or II
R is $C_{3-6}$ cycloalkyl or naphtyl; or
R is

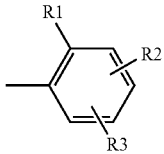

in which R1 is hydrogen, halogen, —$C_{1-6}$alkyl, —$SC_{1-6}$alkyl, —$OC_{1-6}$alkyl, —$NO_2$,
—S(=O)—$C_{1-6}$alkyl, —OH, —$CF_3$, —CN, —$CO_2H$, —$OCF_3$, or —$CO_2C_{1-6}$alkyl;
and R2 and R3 are independently hydrogen, halogen, —$C_{1-6}$ alkyl, —$SC_{1-6}$alkyl, —$OC_{1-6}$alkyl, —$NO_2$, —S(=O)—$C_{1-6}$alkyl, —OH, —$CF_3$, —CN, —$CO_2H$, —$CO_2C_{1-6}$alkyl, —$CONH_2$, —$NH_2$, —$OCH_2(C=O)$OH, —$OCH_2CH_2OCH_3$, —$SO_2NH_2$, —$CH_2SO_2CH_3$, —NH(C=NH)$CH_3$; or R2 and R3 can independently be a radical of the formula

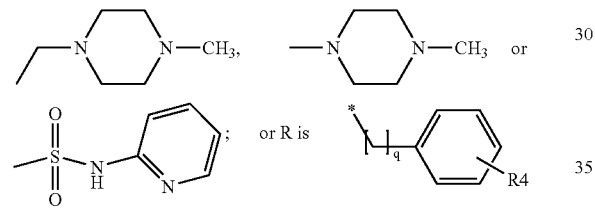

in which q is one or two; R4 is hydrogen, halogen, or —$SO_2NH_2$; or
R is —$(CH_2)_n$—$NR^kR^l$ in which n is 2 or 3, and $R^k$ and $R^l$ are independently —$C_{1-6}$alkyl; or —$NR^kR^l$ together form

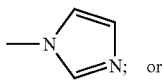

R is

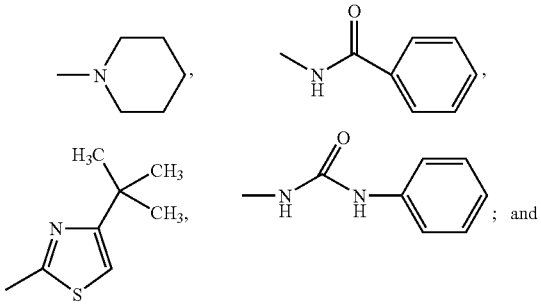

Q is

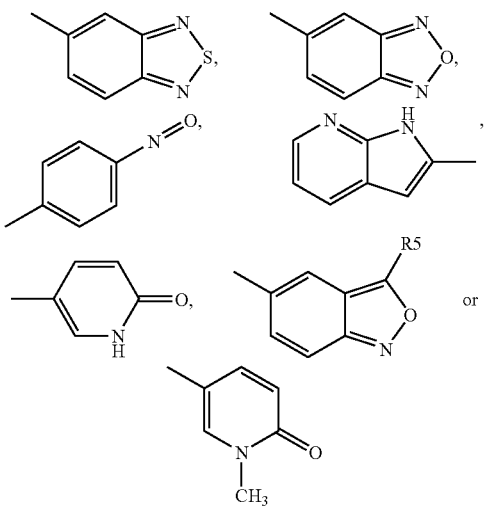

in which R5 is hydrogen, phenyl optionally substituted with up to three $C_{1-6}$ alkyl or halogen, or $C_{1-6}$ alkyl; or
Q is

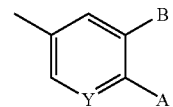

in which Y is CH; and A and B together are a part of

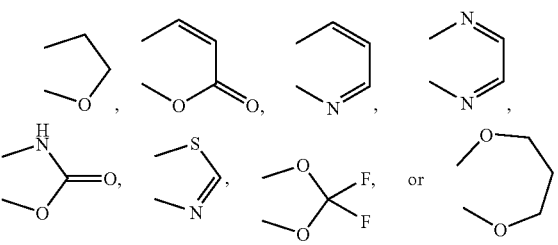

provided that ortho position to Y is N or O.
In another embodiment, R radical of compounds of formula I and II are

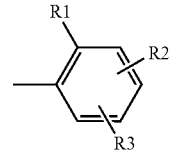

in which R1 is halogen, —$C_{1-6}$alkyl, —$SC_{1-6}$alkyl, —$OC_{1-6}$ alkyl, —$NO_2$, —S(=O)—$C_{1-6}$alkyl, —OH, —$CF_3$, —CN, —$CO_2H$, or —$CO_2C_{1-6}$alkyl;
and R2 and R3 are independently hydrogen, halogen, —$C_{1-6}$ alkyl, —$SC_{1-6}$alkyl, —$OC_{1-6}$alkyl, —$NO_2$, —S(=O)—$C_{1-6}$alkyl, —OH, —$CF_3$, —CN, —$CO_2H$, —$CO_2C_{1-6}$alkyl, —$NH_2$, or —NH(C=NH)$CH_3$;

and
Q is

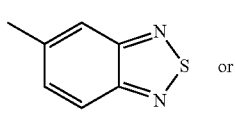 or

Q is

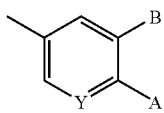

in which Y is CH; and A and B together are a part of

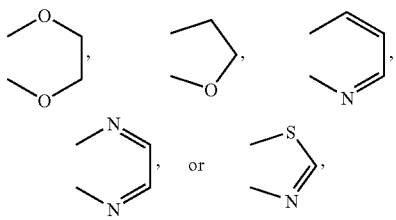 or provided that ortho position to Y is N or O.

Yet in another one embodiment, in formula I or II, R is

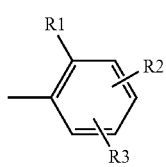

in which R1 is halogen, —C$_{1-6}$alkyl, —SC$_{1-6}$alkyl, —OC$_{1-6}$ alkyl, —NO$_2$, —S(=O)—C$_{1-6}$alkyl, —OH, —CF$_3$, —CN, —CO$_2$H, or —CO$_2$C$_{1-6}$alkyl;

and R2 and R3 are independently hydrogen, halogen, —C$_{1-6}$ alkyl, —SC$_{1-6}$alkyl, —OC$_{1-6}$alkyl, —NO$_2$, —S(=O)—C$_{1-6}$alkyl, —OH, —CF$_3$, —CN, —CO$_2$H, —CO$_2$C$_{1-6}$alkyl, —NH$_2$, or —NH(C=NH)CH$_3$;

and
Q is

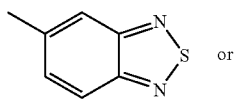 or

Q is

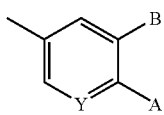

in which Y is CH; and A and B together are a part of

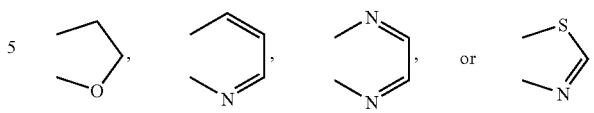

provided that ortho position to Y is N or O.

Yet in a further embodiment, in a compound of formula I or II,

R is

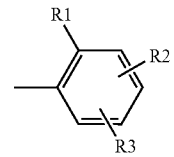

in which R1 is halogen, —C$_{1-6}$alkyl, —SC$_{1-6}$alkyl, —OC$_{1-6}$ alkyl, —NO$_2$, —S(=O)—C$_{1-6}$alkyl, —OH, —CF$_3$, —CN, —CO$_2$H, or —CO$_2$C$_{1-6}$alkyl;

and R2 and R3 are independently hydrogen, halogen, —C$_{1-6}$ alkyl, —SC$_{1-6}$alkyl, —OC$_{1-6}$alkyl, —NO$_2$, —S(=O)—C$_{1-6}$alkyl, —OH, —CF$_3$, —CN, —CO$_2$H, —CO$_2$C$_{1-6}$alkyl, —NH$_2$, or —NH(C=NH)CH$_3$;

and
Q is

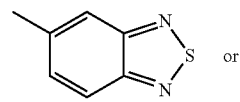 or

Q is

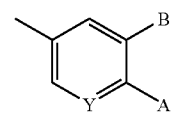

in which Y is CH; and A and B together are a part of

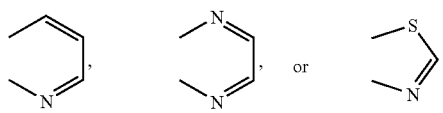

provided that ortho position to Y is N.

In a third aspect of the present invention, there is provided a pharmaceutical composition including a therapeutically effective amount of a compound of formula I or II, or a salt, solvate, or a physiologically functional derivative thereof and one or more of pharmaceutically acceptable carriers, diluents and excipients.

In a fourth aspect of the present invention, there is provided the use of a compound of formula I or II, or a salt, solvate, or a physiologically functional derivative thereof in the preparation of a medicament for use in the treatment or prevention of a disorder of the erythroid and hematopoietic systems mediated the imbalance or inappropriate activity of hYAK3 proteins, including but not limited to, anemias due to renal insufficiency or to chronic disease, such as autoimmunity, HIV, or cancer, and drug-induced anemias, myelodysplastic syndrome, aplastic anemia and myelosuppression, and cytopenia.

In a fifth aspect, the present invention relates to a method of treating or preventing diseases of the erythroid and hematopoietic systems, caused by the hYAK3 imbalance or inappropriate activity including, but not limited to, anemias due to renal insufficiency or to chronic disease, such as autoimmunity, HIV, or cancer, and drug-induced anemias, myelodysplastic syndrome, aplastic anemia and myelosuppression, and cytopenia; comprising administering to a mammal a therapeutically effective amount of a compound of formula I or II, or a salt, solvate, or a physiologically functional derivative thereof and one or more of pharmaceutically acceptable carriers, diluents and excipients.

In a six aspect, the present invention relates to a method of treating or preventing anemias due to renal insufficiency or to chronic disease, such as autoimmunity, HIV, or cancer, and drug-induced anemias, myelodysplastic syndrome, aplastic anemia and myelosuppression, and cytopenia; comprising administering to a mammal a therapeutically effective amount of a compound of formula I or II, or a salt, solvate, or a physiologically functional derivative thereof and one or more of pharmaceutically acceptable carriers, diluents and excipients.

DETAILED DESCRIPTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" refers to a straight or branched chain hydrocarbon. Furthermore, as used herein, the term "$C_{1-6}$ alkyl" refers to an alkyl group as defined above containing at least 1, and at most 6, carbon atoms. Examples of branched or straight chained "$C_{1-6}$ alkyl" groups useful in the present invention include methyl, ethyl, n-propyl, isopropyl, isobutyl, n-butyl, t-butyl, n-pentyl, n-hexyl, and the like.

As used herein, the term "halogen" refers to fluorine (F), chlorine (Cl), bromine (Br), or iodine (I).

As used herein, the term "$C_{3-6}$ cycloalkyl" refers to a non-aromatic cyclic hydrocarbon ring having from three to six carbon atoms. Exemplary "$C_{3-6}$ cycloalkyl" groups include cyclopropyl, cyclobutyl, cyclopentyl, and cyclohexyl.

As used herein, the term "optionally" means that the subsequently described event(s) may or may not occur, and includes both event(s), which occur, and events that do not occur.

As used herein, the crisscrossed double bond indicated by the symbol " " denotes Z and/or E stereochemistry around the double bond. In other words a compound of formula I or II can be either in the Z or E stereochemistry around this double bond, or a compound of formula I or II can also be in a mixture of Z and E stereochemistry around the double bond.

However, in formulas I and II, the preferred compounds have Z stereochemistry around the double bond to which radical Q is attached.

The compounds of formulas I and II naturally may exist in one tautomeric form or in a mixture of tautomeric forms. For example, for sake simplicity, compounds of formula I and II are expressed in one tautomeric form, usually as an exo form, i.e.

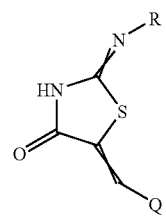

Exo form

However, a person of ordinary skill can readily appreciate, the compounds of formulas I and II can also exist in endo forms.

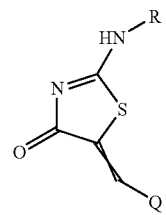

Endo Form

The present invention contemplates all possible tautomeric forms.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula I or II or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

As used herein, the term "substituted" refers to substitution with the named substituent or substituents, multiple degrees of substitution being allowed unless otherwise stated.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by formula I or II above as well as any wholly or partially equilibrated mixtures thereof. The present invention also covers the individual isomers of the compounds represented by the formulas above as mixtures with isomers thereof in which one or more chiral centers are inverted. Also, as stated above, it is understood that all tautomers and mixtures of tautomers are included within the scope of the compounds of formula I or II.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula I or II. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula I or II, as well as salts, solvates and physiological functional derivatives thereof, may be administered as the raw chemical, it is possible to present the active ingredient as a pharmaceutical composition. Accordingly, the invention further provides pharmaceutical compositions (otherwise referred to as pharmaceutical formulations), which include therapeutically effective amounts of compounds of the formula I or II and salts, solvates and physiological functional derivatives thereof, and one or more pharmaceutically acceptable carriers, diluents, or excipients. The compounds of the formula I or II and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula I or II, or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the formula I or II, depending on the condition being treated, the route of administration and the age, weight and condition of the patient, or pharmaceutical formulations may be presented in unit dose forms containing a predetermined amount of active ingredient per unit dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula I or II, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula I or II, and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula I or II for the treatment of or prevention of diseases of the erythroid and hematopoietic systems, caused by hYAK3 imbalance or inappropriate activity including, but not limited to, neutropenia; cytopenia; anemias, including anemias due to renal insufficiency or to a chronic disease, such as autoimmunity or cancer, and drug-induced anemias; polycythemia; and myelosuppression will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula I or II per se. It is envisaged that similar dosages would be appropriate for treatment of the other conditions referred to above.

Method of Preparation

Compounds of general formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula I. Those skilled in the art will recognize if a stereocenter exists in compounds of formula I. Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

More particularly, the compounds of the formula I can be made by the process of either Scheme A or B or a variant thereof. Any person skilled in the art can readily adapt the process of either A or B, such the stoichemistry of the reagents, temperature, solvents, etc. to optimize the yield of the products desired.

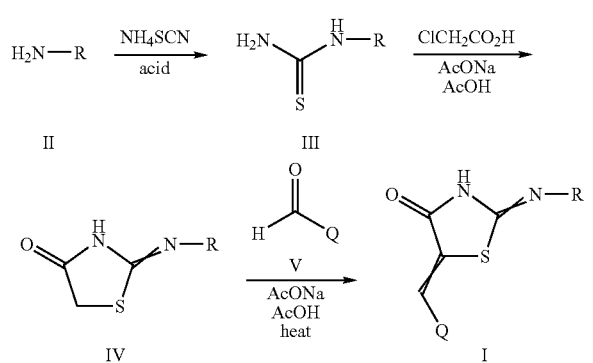

Scheme A

Briefly in Scheme A, a mixture of aniline derivative of formula II (1 equivalent) and NH$_4$SCN (about 1.3 equivalent) in an acid (typically 4N—HCl) is heated to reflux at about 110 C.° for 6 hours. After cooling, the mixture is treated with H$_2$O, which process usually forms a solid, followed by desiccation in vacuo to give a compound of formula III.

A mixture of formula III compound, ClCH$_2$CO$_2$H (1 equivalent), and AcONa (1 equivalent) in AcOH is heated to reflux at around 110 C.° for about 4 h. The mixture is poured onto water thereby a solid is typically formed, which is isolated by filtration. The solid is washed with a solvent such as MeOH to afford a compound of formula IV.

A mixture of formula IV compound, an aldehyde of formula V (1 equivalent), AcONa (3 equivalent) in AcOH is heated to reflux at about 110 C.° for about 10 to 48 hours. After cooling, a small portion of water was added until the solid forms. The solid is filtered and washed with a solvent such as MeOH, followed by desiccation in vacuo to afford a target product of formula I.

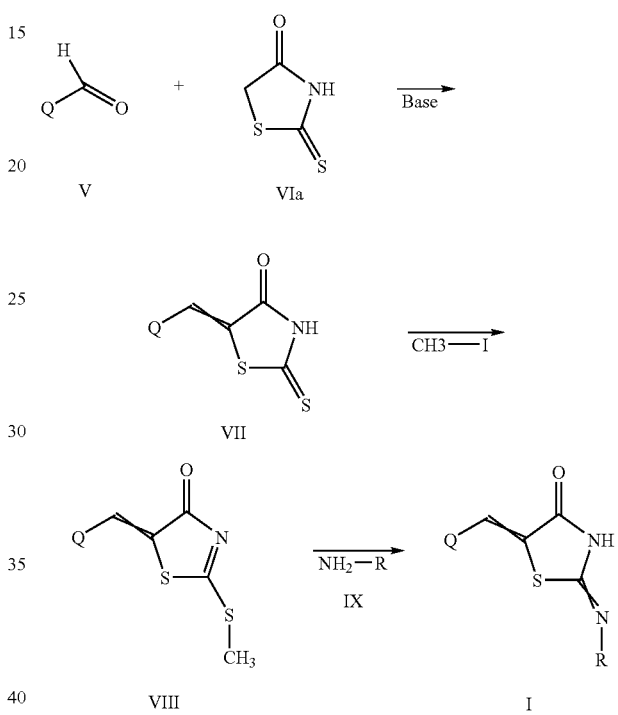

Scheme B

Briefly in Scheme B, a mixture of an aldehyde of formula V (1 equivalent), Rhodanine (1 equivalent), sodium acetate (about 3 equivalents), and acetic acid was heated at around 110 C.° for about 48 h. The reaction mixture is cooled to room temperature to afford a product of formula VII.

Then, to a room temperature suspension of VII (1 equivalent) in a suitable solvent such as ethanol was added Hunig's base (about 2 equivalents) followed by iodomethane (about 5 equivalents). Stirring the resultant suspension at room temperature for 3.5 h will yield a compound of VIII.

To a mixture of VIII (1 equivalent) and MS4A powder was added an amine of formula IX (1-2 equivalent) and ethanol (dehydrated). The mixture was heated by microwave (Smith-Synthesizer-Personal Chemistry) at about 110 C.° for about 1200 seconds. Usually, the desired product of formula I can be obtained in about 20-90% yield after purification.

In Schemes A and B, the meaning of R and Q are as defined in formula I.

All the starting materials are either known, commercially available or can be readily made by a routine method. For example, an aldehyde of formula V in which the radical Q is of the formula

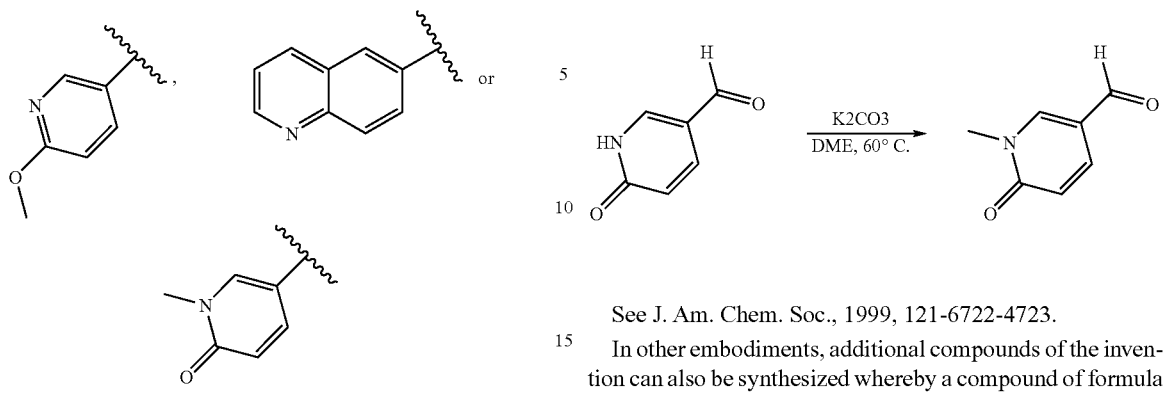

can be readily made by the following standard reaction steps.

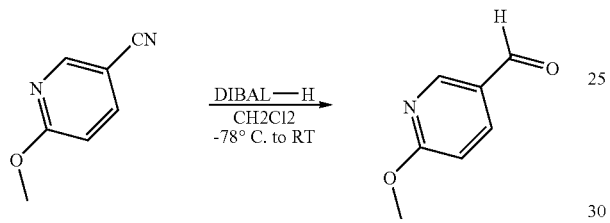

See Eur. J. Org. Chem., 1999, 2609–2621.

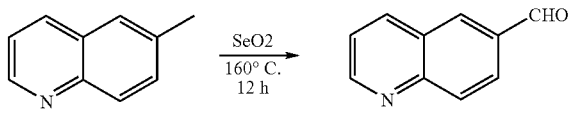

See J. Med. Chem., 2000, 43, 3878-3894.

See J. Am. Chem. Soc., 1999, 121-6722-4723.

In other embodiments, additional compounds of the invention can also be synthesized whereby a compound of formula I are first made by a process of Scheme A or B (or a variant thereof), and Q and R radicals in compounds of formula I thus made are further converted by routine organic reaction techniques into different Q and R groups. For such alternatives, see Schemes C, D and E.

SPECIFIC EMBODIMENTS

Examples

As used herein the symbols and conventions used in these processes, schemes and examples are consistent with those used in the contemporary scientific literature, for example, the Journal of the American Chemical Society or the Journal of Biological Chemistry. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i. v. (intravenous); | Hz (Hertz); |
| MHz (megahertz); | mol (moles); |
| mmol (millimoles); | rt (room temperature); |
| min (minutes); | h (hours); |
| mp (melting point); | TLC (thin layer chromatography); |
| Tr (retention time); | RP (reverse phase); |
| MeOH (methanol); | i-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | AcOEt (ethyl acetate); |
| DME (1,2-dimethoxyethane); | DCM (dichloromethane); |
| DCE (dichloroethane); | DMF (N,N-dimethylformamide); |
| DMPU (N,N'-dimethylpropyleneurea); | (CDI (1,1-carbonyldiimidazole); |
| IBCF (isobutyl chloroformate); | HOAc (acetic acid); |
| HOSu (N-hydroxysuccinimide); | HOBT (1-hydroxybenzotriazole); |
| mCPBA (meta-chloroperbenzoic acid; | EDC (ethylcarbodiimide hydrochloride); |
| BOC (tert-butyloxycarbonyl); | FMOC (9-fluorenylmethoxycarbonyl); DCC |
| (dicyclohexylcarbodiimide); | CBZ (benzyloxycarbonyl); |
| Ac (acetyl); | atm (atmosphere); |
| TMSE (2-(trimethylsilyl)ethyl); | TMS (trimethylsilyl); |
| TIPS (triisopropylsilyl); | TBS (t-butyldimethylsilyl); |
| DMAP (4-dimethylaminopyridine); | BSA (bovine serum albumin) |
| ATP (adenosine triphosphate); | HRP (horseradish peroxidase); |

-continued

DMEM (Dulbecco's modified Eagle medium);
HPLC (high pressure liquid chromatography);
BOP (bis(2-oxo-3-oxazolidinyl)phosphinic chloride);
TBAF (tetra-n-butylammonium fluoride);
HBTU (O-Benzotriazole-1-yl-N,N,N',N'-tetramethyluronium hexafluorophosphate).
HEPES (4-(2-hydroxyethyl)-1-piperazine ethane sulfonic acid);
DPPA (diphenylphosphoryl azide);
fHNO3 (fumed HNO3); and
EDTA (ethylenediaminetetraacetic acid).

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted.

$^1$H NMR spectra were recorded on a Varian VXR-300, a Varian Unity-300, a Varian Unity-400 instrument, a Brucker AVANCE-400, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Low-resolution mass spectra (MS) were recorded on a JOEL JMS-AX505HA, JOEL SX-102, or a SCIEX-APIii spectrometer; LC-MS were recorded on a micromass 2MD and Waters 2690; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck).

For ease of illustration, the regiochemistry around the double bonds in the chemical formulas in the Examples are drawn as fixed for ease of representation; however, a skilled in the art will readily appreciate that the compounds will naturally assume more thermodynamically stable structure around the C=N (the imine) double bond if it exits as exo form. Further compounds can also exit in endo form. As stated before, the invention contemplates both endo and exo forms as well as both regioisomers around the exo imine bond. Further it is intended that both E and Z isomers are encompassed around the C=C double bond.

Example 1

2-(2-Chloro-5-fluoro-phenylimino)-5-(2,3-dihydro-benzofuran-5-ylmethylene)-thiazolidin-4-one

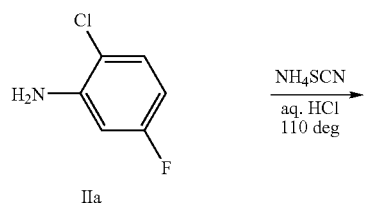

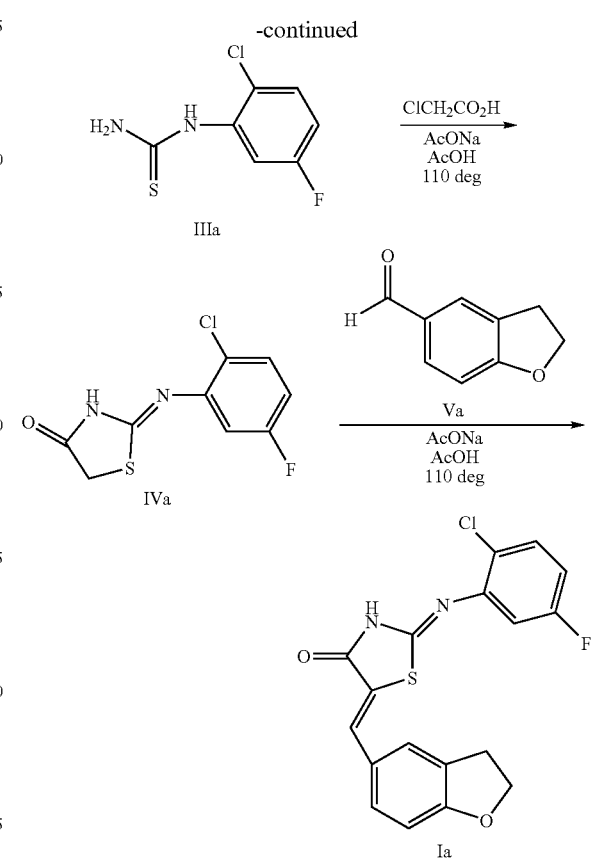

A mixture of 2-chloro-5-fluoroaniline IIa (2.0 g, 13.7 mmol) and 1.7 g of NH$_4$SCN in 4N—HCl (20 mL) was heated to reflux at 110 C.° for 6 hours. After cooling, it was treated with H$_2$O to form a solid, followed by desiccation in vacuo to give thiourea IIIa (870 mg, 4.3 mmol). A mixture of IIIa (870 mg, 4.3 mmol), ClCH$_2$CO$_2$H (400 mg), and AcONa (350 mg) in AcOH (5 mL) was heated to reflux at 110 C.° for 4 h. The mixture was poured onto water and the formed solid was isolated by filtration. It was washed with MeOH to give imino thiazolidinone IVa (456 mg, 1.9 mmol). A mixture of IVa (98 mg, 0.4 mmol), aldehyde Va (60 mg, 0.4 mmol), AcONa (100 mg) in AcOH (2 mL) was heated to reflux at 120 degree for 48 hours. After cooling, a small portion of water was added until the solid forms. It was filtered and washed with MeOH, followed by desiccation in vacuo to afford a target product Ia (61 mg, 0.16 mmol).

$^1$HNMR: (DMSO-d$_6$) δ 3.21 (t, 2H), 4.58 (t, 2H), 6.87 (d, 1H), 7.06 (sbr, 2H), 7.30 (d, 1H), 7.39 (s, 1H), 7.58 (sbr, 2H), 12.60 (sbr, 1H): LC/MS: m/z 375 (M+1), 377 (M+3)

Compounds in Examples 2-61, 73-94, and 96 were made by the process described in Scheme A, analogous to the method described in Example 1.

Example 2

2-(2-Chloro-phenylimino)-5-(2-oxo-2H-chromen-6-ylmethylene)-thiazolidin-4-one

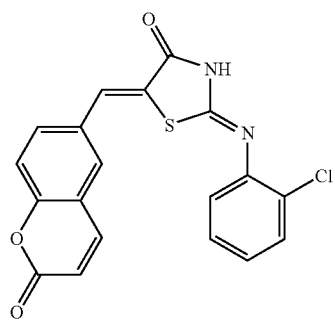

$^1$H NMR (DMSO-d$_6$) δ 6.52 (d, 1H), 7.15 (d, 1H), 7.21 (t, 1H), 7.38 (t, 1H), 7.49 (d, 1H), 7.54 (d, 1H), 7.72 (s, 1H), 7.71-7.74 (m, 1H), 7.85 (s, 1H), 8.13 (d, 1H), 12.73 (s br, 1H): LC/MS: m/z 383 (M+1), 385 (M+3)

Example 3

2-(2-Chloro-phenylimino)-5-(2-oxo-2H-chromen-6-ylmethylene)-thiazolidin-4-ne

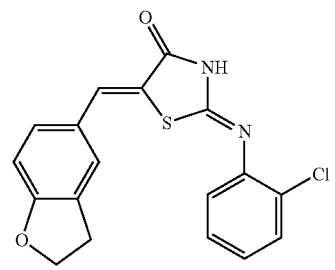

$^1$H NMR (DMSO-d$_6$) δ 3.19 (t, 2H), 4.58 (t, 2H), 6.87 (d, 1H), 71-6 (d, 1H), 7.20 (t, 1H), 7.28 (d, 1H), 7.37 (m, 2H), 7.54 (d, 1H), 7.61 (s, 1H), 12.54 (brs, 1H): LC/MS: m/z 357 (M+1), 359(M+3)

Example 4

2-(2-Chloro-phenylimino)-5-(2-oxo-2H-chromen-6-ylmethylene)-thiazolidin-4-one

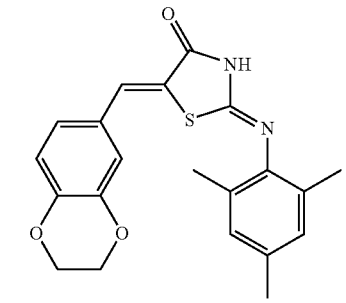

$^1$H NMR (DMSO-d$_6$) δ 2.06 (s, 6H), 2.25 (s, 3H), 4.24 (dd, 4H), 6.94 (m, 4H), 6.96 (s, 1H), 7.52 (s, 1H), 12.5 (brs, 1H): LC/MS: m/z 381 (M+1)

Example 5

5-(2,3-Dihydro-benzofuran-5-ylmethylene)-2-(2,4,6-trimethyl-phenylimino)-thiazolidin-4-one

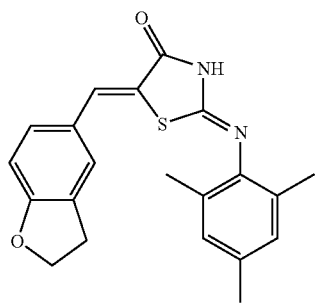

$^1$H NMR (DMSO-d$_6$) δ 2.05 (s, 6H), 2.24 (s, 3H), 3.19 (t, 2H), 4.56 (t, 2H), 6.84 (d, 1H), 6.91 (m, 2H), 7.22 (d, 1H), 7.31 (s, 1H), 7.51 (s, 1H), 12.5 (brs, 1H):LC/MS:m/z 365 (M+1)

Example 6

2-Cyclohexylimino-5-(2,3-dihydro-benzo[1-6]dioxin-6-ylmethylene)-thiazolidin-4-one

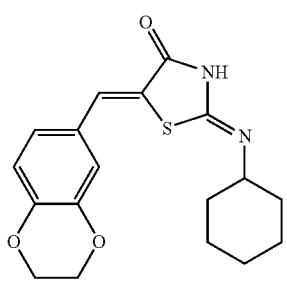

¹H NMR (DMSO-d₆) δ 1.18 (sbr, 1H), 1.31 (mbr, 2H), 1.59 (dbr, 1H), 1.72 (sbr, 2H), 1.93 (sbr, 2H), 3.89 (brs, 1H), 6.99 (d, 1H), 7.05 (m, 2H), 7.48 (s, 1H), 9.50 (dbr, 1H):LC/MS:n/z 345 (M+1)

Example 7

2-Cyclohexylimino-5-(2,3-dihydro-benzofuran-5-ylmethylene)-thiazolidin-4-one

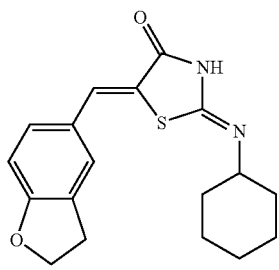

¹H NMR (DMSO-d₆) δ 1.19 (mbr, 1H), 1.29 (mbr, 2H), 1.57 (dbr, 1H), 1.72 (sbr, 2H), 1.91 (mbr, 2H), 3.24 (t, 2H), 3.89 (sbr, 1H), 4.60 (t, 2H), 6.91 (d, 1H), 7.33 (d, 1H), 7.43 (s, 1H), 7.53 (s, 1H), 9.45 (d, 1H): LC/MS: m/z 329 (M+1)

Example 8

5-Benzo[1,3]dioxol-5-ylmethylene-2-(2-chloro-phenylimino)-thiazolidin-4-one

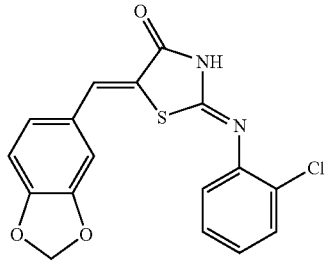

¹H NMR (DMSO-d₆) δ 6.08 (d, 2H), 7.03 (m, 2H), 7.07 (s, 1H), 7.13 (d, 1H), 7.19 (t, 1H), 7.36 (t, 1H), 7.53 (d, 1H), 7.58 (s, 1H), 12.54 (sbr, 1H): LC/MS: m/z 359 (M+1), 361 (M+3)

Example 9

5-(2,3-Dihydro-benzofuran-5-ylmethylene)-2-o-tolylimino-thiazolidin-4-one

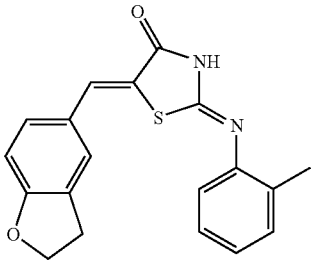

¹H NMR (DMSO-d₆) δ 2.14 (s, 3H), 3.19 (t, 2H), 4.57 (t, 2H), 6.86 (d, 1H), 6.93 (d, 1H), 7.10 (t, 1H), 7.22 (t, 1H), 7.27 (m, 2H), 7.35 (s, 1H), 7.57 (s, 1H), 12.24 (sbr, 1H): LC/MS: m/z 337 (M+1)

Example 10

5-(2,3-Dihydro-benzo[1-6]dioxin-6-ylmethylene)-2-o-tolylino-thiazolidin-4-one

¹H NMR (DMSO-d₆) δ 2.14 (s, 3H), 4.23 (d, 2H), 4.26 (d, 2H), 6.96 (m, 2H), 7.00 (s, 1H), 7.11 (t, 1H), 7.22 (t, 1H), 7.29 (d, 1H), 7.53 (s, 1H), 12.29 (sbr, 1H): LC/MS: m/z 353 (M+1)

Example 11

5-[2-(2-Chloro-phenylimino)-4-oxo-thiazodin-5-ylidenemethyl]-3H-benzooxazol-2-one

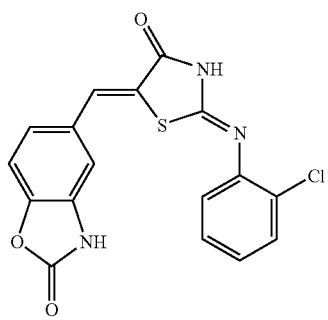

¹H NMR (DMSO-d₆) δ 7.14 (d, 1H), 7.18 (s, 1H), 7.20 (t, 1H), 7.28 (d, 1H), 7.38 (m, 2H), 7.54 (d, 1H), 7.69 (s, 1H), 12.10 (sbr, 1H): LC/MS: m/z 372 (M+1), 374 (M+3)

Example 12

2-(2-Bromo-phenylimino)-5-(2,3-dihydro-benzofuran-5-ylmethylene)-thiazolidin-4-one

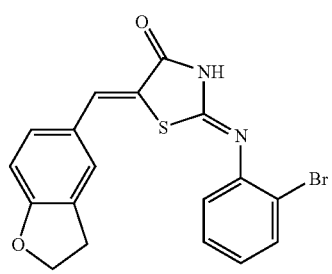

¹H NMR (DMSO-d₆) δ 3.19 (t, 2H), 4.57 (t, 2H), 6.87 (d, 1H), 7.11 (m, 2H), 7.28 (d, 1H), 7.36 (s, 1H), 7.40 (t, 1H), 7.60 (s, 1H), 7.69 (d, 1H), 12.51 (sbr, 1H): LC/MS: m/z 401(M), 403 (M+2)

Example 13

2-(2-Trifluoromethyl-phenylimino)-5-(2,3-dihydro-benzofuran-5-ylmethylene)-thiazolidin-4-one

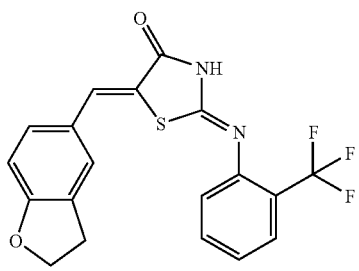

¹H NMR (DMSO-d₆) δ 3.19 (t, 2H), 4.58 (t, 2H), 6.87 (d, 1H), 7.22 (d, 1H), 7.29 (d, 1H), 7.36 (m, 2H), 7.62 (s, 1H), 7.69 (t, 1H), 7.75 (d, 1H), 12.58 (sbr, 1H): LC/MS: m/z 391 (M+1)

Example 14

2-(2,6-Dichloro-phenylimino)-5-(2,3-dihydro-benzofuran-5-ylmethylene)-thiazolidin-4-one

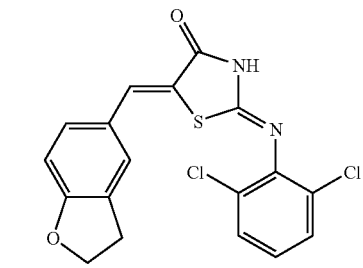

¹H NMR (DMSO-d₆) δ 3.20 (t, 2H), 4.58 (t, 2H), 6.87 (d, 1H), 7.20 (t, 1H), 7.28 (d, 1H), 7.36 (s, 1H), 7.55 (d, 1H), 7.64 (s, 1H), 12.77 (sbr, 1H): LC/MS: m/z 391 (M+1), 393 (M+3)

Example 15

5-(2,3-Dihydro-benzofuran-5-ylmethylene)-2-(2-methylsulfanyl-phenylimino)-thiazolidin-4-one

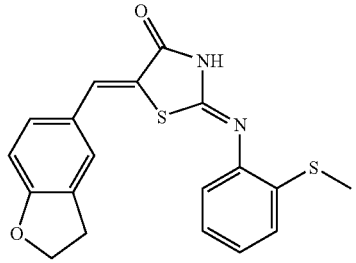

¹H NMR (DMSO-d₆) δ 2.38 (s, 3H), 3.19 (t, 2H), 4.57 (t, 2H), 6.85 (d, 1H), 6.93 (d, 1H), 7.17 (m, 2H), 7.25 (m, 2H), 7.35 (s, 1H), 7.52 (s, 1H), 12.32 (sbr, 1H): LC/MS: m/z 369 (M+1)

Example 16

5-(2,3-Dihydro-benzofuran-5-ylmethylene)-2-(2-fluoro-phenylimino)-thiazolidin-4-one

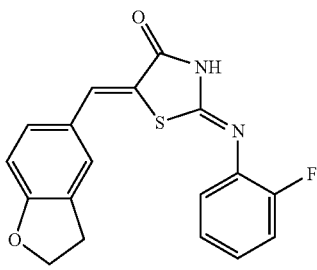

¹H NMR (DMSO-d₆) δ 3.20 (t, 2H), 4.58 (t, 2H), 6.88 (d, 1H), 7.15 (m, 1H), 7.21 (m, 2H), 7.29 (m, 2H), 7.38 (s, 1H), 7.61 (s, 1H): LC/MS: m/z 341 (M+1)

Example 17

2-(2-Methylsulfanyl-phenylimino)-5-(quinolin-6-ylmethylene)-thiazolidin-4-one

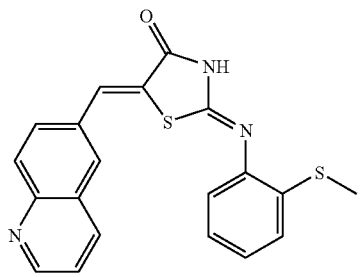

$^1$H NMR (DMSO-d$_6$) δ 2.40 (s, 3H), 6.99 (d, 1H), 7.17-7.30 (m, 3H), 7.56 (dd, 1H), 7.83 (m, 2H), 8.08 (d, 1H), 8.13 (s, 1H), 8.46 (d, 1H), 8.92 (m, 1H), 12.65 (sbr, 1H):LC/MS: m/z 378 (M+1)

Example 18

2-(2-Bromo-phenylimino)-5-(quinolin-6-ylmethylene)-thiazolidin-4-one

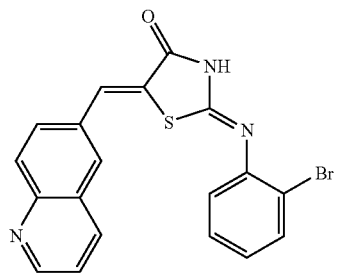

$^1$H NMR (DMSO-d$_6$) δ 7.15 (t, 2H), 7.43 (t, 1H), 7.56 (dd, 1H), 7.71 (d, 1H), 7.83 (s, 1H), 7.86 (s, 1H), 8.08 (d, 1H), 81-6 (s, 1H), 8.44 (d, 1H), 8.93 (m, 1H), 12.77 (brs, 1H): LC/MS: m/z 410 (M), 412 (M+2)

Example 19

2-(2,3-Dimethyl-phenylimino)-5-(quinolin-6-ylmethylene)-thiazolidin-4-one

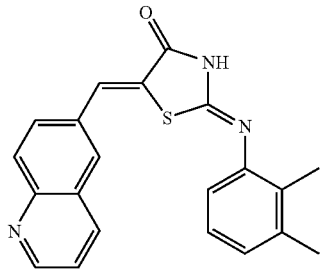

$^1$H NMR (DMSO-d$_6$) δ 2.07 (s, 3H), 2.27 (s, 3H), 6.81 (d, 1H), 7.03 (d, 1H), 7.12 (t, 1H), 7.55 (dd, 1H), 7.78 (s, 1H), 7.83 (dd, 1H), 8.06 (d, 1H), 8.11 (s, 1H), 8.42 (d, 1H), 8.92 (m, 1H): LC/MS: m/z 360 (M+1)

Example 20

2-(Naphthalen-1-ylimino)-5-(quinolin-6-ylmethylene)-thiazolidin-4-one

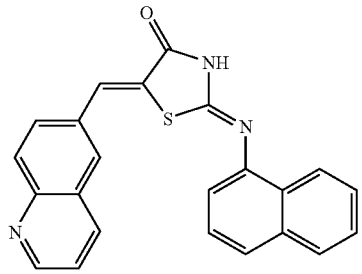

$^1$H NMR (DMSO-d$_6$) δ 7.17 (d, 1H), 7.54 (m, 4H), 7.80 (m, 2H), 7.82 (s, 1H), 7.97 (t, 2H), 8.03 (d, 1H), 8.09 (s, 1H), 8.38 (d, 1H), 8.90 (m, 1H): LC/MS: m/z 382 (M+1)

Example 21

5-(Quinolin-6-ylmethylene)-2-(2-trifluoromethyl-phenylimino)-thiazolidin-4-one

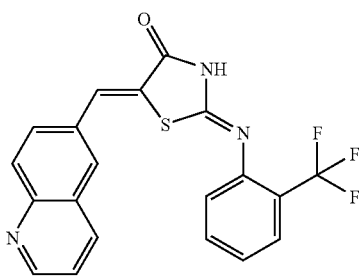

$^1$H NMR (DMSO-d$_6$) δ 7.23 (d, 1H), 7.36 (t, 1H), 7.55 (dd, 1H), 7.69 (t, 1H), 7.75 (d, 1H), 7.81 (s, 1H), 7.85 (d, 1H), 8.06 (d, 1H), 8.12 (s, 1H), 8.44 (d, 1H), 8.92 (d, 1H), 12.80 (sbr, 1H): LC/MS: m/z 400 (M+1)

Example 22

2-(2-Chloro-5-trifluoromethyl-phenylimino)-5-quinolin-6-ylmethylene-thiazolidin-4-one

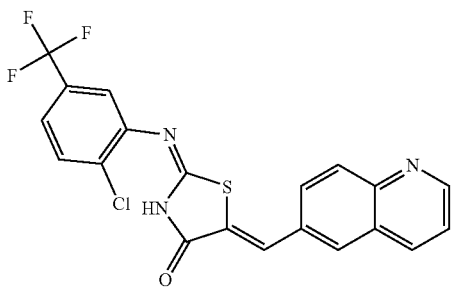

$^1$H NMR (DMSO-d$_6$) δ 7.50-7.60 (mbr, 2H), 7.56 (dd, 1H), 7.70-7.95 (mbr, 3H), 8.07 (d, 1H), 81-6 (s, 1H), 8.44 (d, 1H), 8.92 (m, 1H), 12.89 (sbr, 1H): LC/MS: m/z 434 (M+1), 436 (M+3)

Example 23

2-(2,6-Dichloro-phenylimino)-5-8quinolin-6-ylmethylene)-thiazolidin-4-one

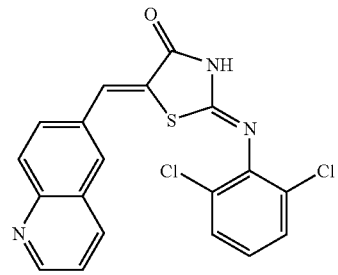

$^1$H NMR (DMSO-d$_6$) δ 7.23 (t, 1H), 7.55 (m, 3H), 7.84 (d, 1H), 7.87 (s, 1H), 8.08 (d, 1H), 81-6 (s, 1H), 8.46 (d, 1H), 8.93 (m, 1H), 13.01 (sbr, 1H):LC/MS: m/z 400 (M+1), 402 (M+3)

Example 24

2-(2-Bromo-phenylimino)-5-(2,3-dihydro-benzo[1-6]dioxin-6-ylmethylene)thiazolidin-4-one

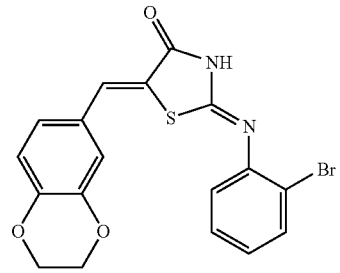

$^1$H NMR (DMSO-d$_6$) δ 4.25 (m, 4H), 6.97 (m, 3H), 7.13 (t, 2H), 7.42 (t, 1H), 7.57 (s, 1H), 7.70 (d, 1H), 12.60 (sbr, 1H): LC/MS: m/z 417 (M), 419 (M+2)

Example 25

5-(Benzo[1,3]dioxol-5-ylmethylene)-2-(2-bromo-phenylimino)-thiazolidin-4-one

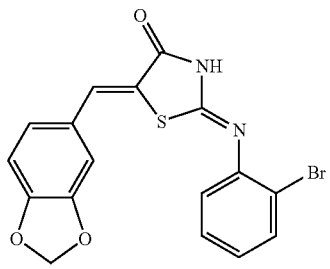

$^1$H NMR (DMSO-d$_6$) δ 6.09 (s, 2H), 7.03 (m, 3H), 7.13 (m, 2H), 7.41 (t, 1H), 7.60 (s, 1H), 7.69 (d, 1H), 12.60 (sbr, 1H) 403

Example 26

2-(2-Chloro-phenylimino)-5-(quinoxalin-6-ylmethylene)-thiazolidin-4-one

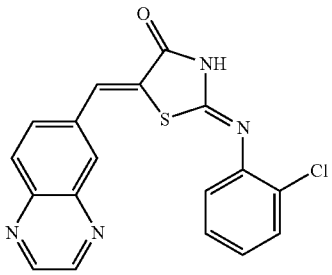

$^1$H NMR (DMSO-d$_6$) δ 7.19 (d, 1H), 7.23 (t, 1H), 7.39 (t, 1H), 7.56 (d, 1H), 7.92 (s, 1H), 7.98. (dd, 1H), 8.17 (m, 2H), 8.97 (s, 2H), 12.84 (sbr, 1H): LC/MS: m/z 367 (M+1), 369 (M+3)

Example 27

2-(2,6-Dichloro-phenylimino)-5-(2,3-dihydro-benzo[1-6]dioxin-6-ylmethylene)-thiazolidin-4-one

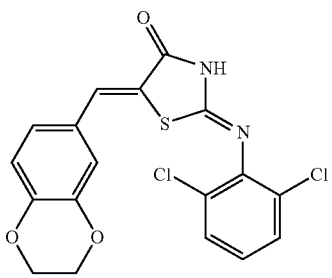

¹H NMR (DMSO-d₆) δ 4.25 (m, 4H), 6.97 (s, 2H), 7.02 (s, 1H), 7.22 (t, 1H), 7.55 (d, 2H), 7.60 (s, 1H), 12.84 (sbr, 1H): LC/MS: m/z 407 (M+1), 409 (M+3)

Example 28

5-(2,3-Dihydro-benzo[1-6]dioxin-6-ylmethylene)-2-(2-nitro-phenylimino)thiazolidin-4-one

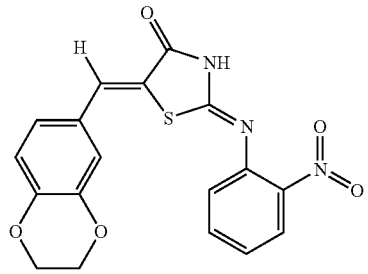

¹H NMR (DMSO-d₆) δ 4.26 (m, 4H), 6.96 (d, 1H), 7.03 (m, 2H), 7.31 (d, 1H), 7.38 (t, 1H), 7.58 (s, 1H), 7.72 8t, 1H), 8.01 (d, 1H), 12.66 (sbr, 1H): LC/MS: m/z 384 (M+1)

Example 29

5-(2,3-Dihydro-benzofuran-5-ylmethylene)-2-(2-nitro-phenylimino)-thiazolidin-4-one

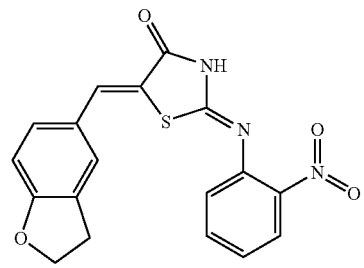

¹H NMR (DMSO-d₆) δ 3.20 (t, 2H), 4.58 (t, 2H), 6.88 (d, 1H), 7.30 (d, 2H), 7.39 (m, 2H), 7.64 (s, 1H), 7.73 (t, 1H), 8.03 (d, 1H), 12.63 (sbr, 1H): LC/MS: m/z 368 (M+1)

Example 30

2-(2-Chloro-4-fluoro-5-methyl-phenylimino)-5-(2,3-dihydro-benzofuran-5-ylmethylene)-thiazolidin-4-one

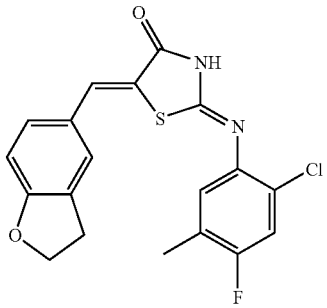

¹H NMR (DMSO-d₆) δ 2.22 (s, 3H), 3.20 (t, 2H), 4.58 (t, 2H), 6.87 (d, 1H), 7.05 (d, 1H), 7.28 (d, 1H), 7.38 (s, 1H), 7.44 (d, 1H), 7.58 (s, 1H), 12.43 (sbr, 1H): LC/MS: m/z 389 (M+1), 391 (M+3)

Example 31

3-Chloro-4-[5-(2,3-dihydro-benzofuran-5-ylmethylene)-4-oxo-thiazolidin-2-ylideneamino]-benzoic acid mehyl ester

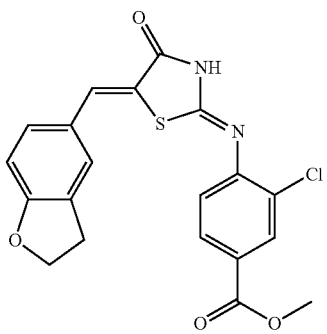

¹H NMR (DMSO-d₆) δ 3.20 (t, 2H), 3.87 (s, 3H), 4.57 (t, 2H), 6.85 (d, 1H), 7.29 (d, 1H), 7.38 (mbr, 2H), 7.52 (s, 1H), 7.88 (d, 1H), 7.99 (s, 1H), 12.4 (sbr, 1H): LC/MS: m/z 415 (M+1), 417 (M+3)

Example 32

2-(2-Chloro-phenylimino)-5-(2,3-dihydro-benzo[1-6]dioxin-6-ylmethylene)-thiazolidin-4-one

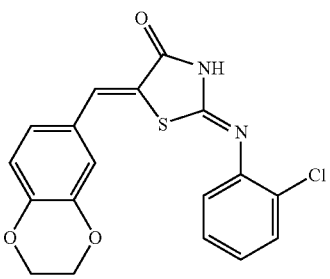

¹H NMR (DMSO-d₆) δ 4.25 (dd, 4 H), 6.94-7.01 (m, 3H), 71-6 (d, 1H), 7.20 (t, 1H), 7.37 (t, 1H), 7.54 (d, 1H), 7.57 (s, 1H), 12.6 (s br, 1H): LC/MS: m/z 373 (M+1), 3.75 (M+3)

Example 33

2-(2-Chloro-4-trifluoromethyl-phenylimino)-5-(2,3-dihydro-benzofuran-5-ylmethylene)-thiazolidin-4-one

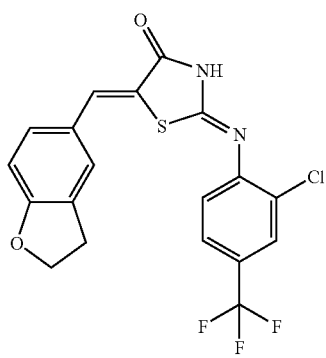

¹H NMR (DMSO-d₆) δ 3.20 (t, 2H), 4.58 (t, 2H), 6.87 (d, 1H), 7.30 (d, 1H), 7.37 (m, br), 7.40 (s, 1H), 7.62 (s, 1H), 7.73 (d, 1H), 7.95 (s, 1H), 12.68 (sbr, 1H):LC/MS:m/z 425 (M+1), 427 (M+3)

Example 34

2-(4-Bromo-2-chloro-phenylimino)-5-(2,3-dihydro-benzofuran-5-ylmethylene)-thiazolidin-4-one

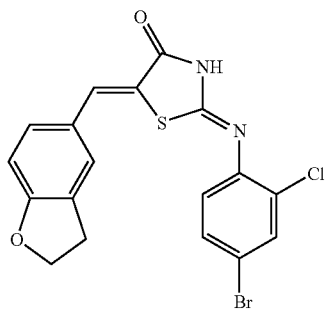

¹H NMR (DMSO-d₆) δ 3.20 (t, 2H), 4.57 (t, 2H), 6.85 (d, 1H), 7.07 (sbr, 1H), 7.28 (d, 1H), 7.37 (s, 1H), 7.51 (mbr, 2H), 7.76 (mbr, 1H), 12.07 (sbr, 1H): LC/MS: m/z 436 (M+1)

Example 35

5-(2,3-Dihydro-benzofuran-5-ylmethylene)-2-(2-methanesulfinyl-phenylimino)-thiazolidin-4-one

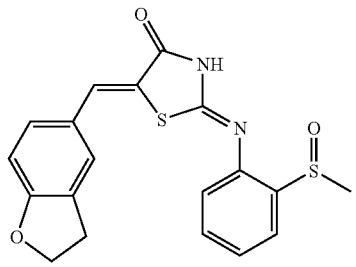

¹H NMR (DMSO-d₆) δ 2.68 (s, 3H), 3.20 (t, 2H), 4.58 (t, 2H), 6.87 (d, 1H), 7.18 (d, 1H), 7.31 (d, 1H), 7.39 (s, 1H), 7.46 (t, 1H), 7.57 (t, 1H), 7.63 (s, 1H), 7.80 (d, 1H):LC/MS:m/z 385 (M+1)

Example 36

3-Chloro-4-[5-(2,3-dihydro-benzofuran-5-ylmethylene)-4-oxo-thiazolidin-2-ylideneamino]-benzoic acid

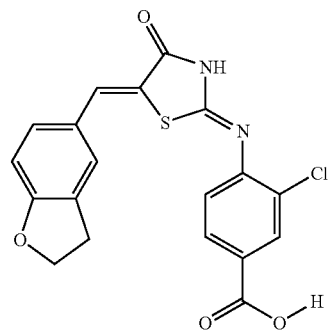

¹H NMR (DMSO-d₆) δ 3.20 (t, 2H), 4.55 (t, 2H), 6.82 (d, 1H), 7.25 (d, 1H), 7.28 (mbr, 2H), 7.36 (s, 1H), 7.73 (d, 1H), 7.86 (s, 1H): LC/MS: m/z 401 (M+1), 403 (M+3)

Example 37

5-[2-(2-Chloro-phenylimino)-4-oxo-thiazolidin-5-ylidenemethyl]-1H-pyridin-2-one

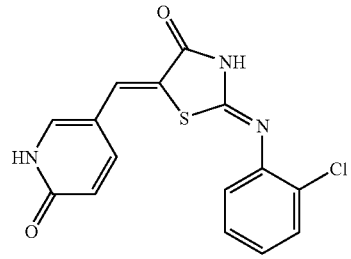

¹H NMR (DMSO-d₆) δ 6.40 (m, 1H), 7.07 (d, 1H), 7.13 (t, 1H), 7.32 (t, 1H), 7.38 (s, 1H), 7.50 (t, 2H), 7.77 (s, 1H), 12.07 (sbr, 1H): LC/MS: m/z 332 (M+1), 334 (M+3)

Example 38

2-(2-Methylsulfanyl-phenylimino)-5-(quinolin-6-ylmethylene)-thiazolidin-4-one

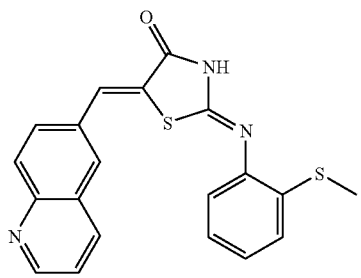

¹H NMR (DMSO-d₆) δ 2.40 (s, 3H), 7.17-7.28 (m, 3H), 7.55 (dd, 1H), 7.80 (s, 1H), 7.84 (d, 1H), 8.07 (d, 1H), 8.12 (s, 1H), 8.42 (d, 1H), 8.92 (m, 1H), 12.56 (sbr, 1H):LC/MS:m/z 378 (M+1)

Example 39

2-(2-Chloro-4-fluoro-5-methyl-phenylimino)-5-(quinolin-6-ylmethylene)-thiazolidin-4-one

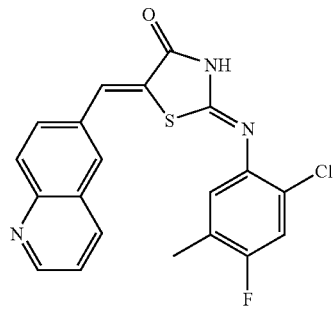

¹H NMR (DMSO-d₆) δ 2.23 (s, 3H), 7.10 (d, 1H), 7.48 (d, 1H), 7.57 (dd, 1H), 7.83 (s, 1H), 7.86 (dd, 1H), 8.08 (d, 1H), 81-6 (s, 1H), 8.46 (d, 1H), 8.93 (m, 1H), 12.69 (sbr, 1H): LC/MS: m/z 398 (M+1), 400 (M+3)

Example 40

2-(2-Chloro-5-fluoro-phenylimino)-5-(quinolin-6-ylmethylene)-thiazolidin-4-one

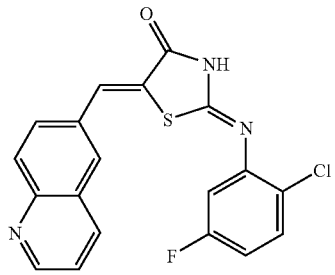

¹H NMR (DMSO-d₆) δ 7.10 (sbr, 2H), 7.56 (dd, 1H), 7.58 (mbr, 1H), 7.82 (s, 1H), 7.88 (m, 1H), 8.07 (d, 1H), 81-6 (s, 1H), 8.46 (d, 1H), 8.93 (d, 1H), 12.81 (sbr, 1H):LC/MS:m/z 384 (M+1), 386 (M+3)

Example 41

2-(2-Chloro-5-fluoro-phenylimino)-5-(2,3-dihydro-benzo[1-6]dioxin-6-ylmethylene)-thiazolidin-4-one

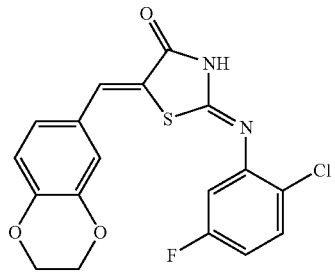

¹H NMR (DMSO-d₆) δ 4.26 (m, 4H), 6.95 (d, 1H), 7.02 (d, 1H), 7.05 (mbr, 3H), 7.55 (mbr, 2H), 12.65 (sbr, 1H): LC/MS: m/z 391 (M+1), 393 (M+3)

Example 42

2-(2-Chloro-4-trifluoromethyl-phenylimino)-5-quinolin-6-ylmethylene-thiazolidin-4-one

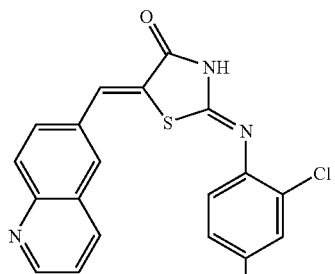

¹H NMR (DMSO-d₆) δ 7.41 (d, 1H), 7.57 (dd, 1H), 7.76 (d, 1H), 7.87 (m, 2H), 7.99 (s, 1H), 8.08 (d, 1H), 8.17 (s, 1H), 8.47 (d, 1H), 8.94 (dd, 1H), 12.90 (sbr, 1H): LC/MS: n/z 435 (M+1), 437 (M+3)

Example 43

5-(Benzothiazol-6-ylmethylene)-2-(2-chloro-phenylimino)-thiazolidin-4-one

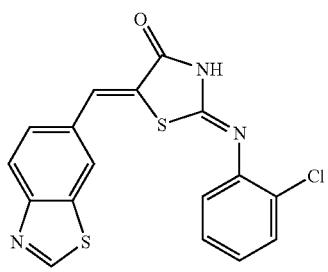

¹H NMR (DMSO-d₆) δ 7.14 (d, 1H), 7.20 (t, 1H), 7.37 (t, 1H), 7.53 (d, 1H), 7.65 (d, 1H), 7.77 (s, 1H), 81-6 (d, 1H), 8.36 (s, 1H), 9.47 (s, 1H), 12.61 (sbr, 1H): LC/MS: n/z 372 (M+1), 374 (M+3)

Example 44

5-(Benzo[1,2,5]thiadiazol-5-ylmethylene)-2-(2-bromo-phenylimino)-thiazolidin-4-one

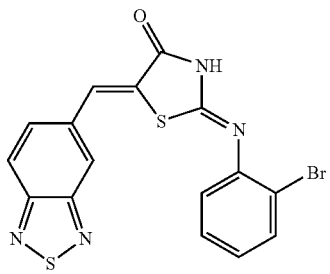

¹H NMR (DMSO-d₆) δ 7.15 (m, 2H), 7.43 (t, 1H), 7.71 (d, 1H), 7.83 (dd, 1H), 7.89 (s, 1H), 8.16 (d, 1H), 8.22 (s, 1H), 12.83 (sbr, 1H): LC/MS: m/z 417 (M), 419 (M+2)

Example 45

5-(Benzo[1,2,5]thiadiazol-5-ylmethylene)-2-(2-chloro-5-fluoro-phenylimino)-thiazolidin-4-one

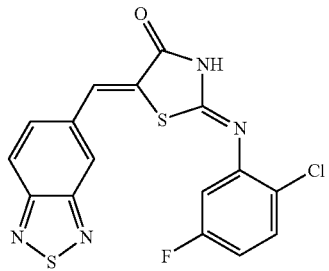

¹H NMR (DMSO-d₆) δ 7.11 (m, 2H), 7.60 (t, 1H), 7.85 (d, 1H), 7.89 (s, 1H), 8.16 (d, 1H), 8.25 (s, 1H), 12.89 (sbr, 1H): LC/MS: m/z 391 (M+1), 393 (M+3)

Example 46

5-(Benzothiazol-6-ylmethylene)-2-(2,6-dichloro-phenylimino)-thiazolidin-4-one

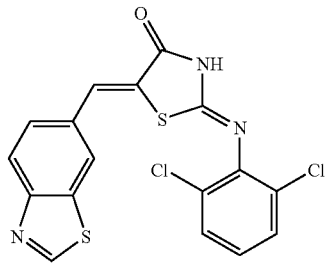

¹H NMR (DMSO-d₆) δ 7.23 (t, 1H), 7.57 (d, 2H), 7.66 (d, 1H), 7.86 (s, 1H), 8.15 (d, 1H), 8.39 (s, 1H), 9.49 (s, 1H), 12.98 (sbr, 1H): LC/MS: m/z 406 (M+1), 408 (M+3)

Example 47

2-(2-Chloro-phenylimino)-5-(4-hydroxy-3-nitro-benzylidene)-thiazolidin-4-one

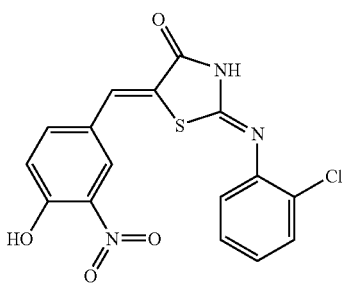

¹H NMR (DMSO-d₆) δ 7.14 (d, 1H), 7.22 (m, 2H), 7.38 (t, 1H), 7.54 (d, 1H), 7.62 (d, 1H), 7.67 (s, 1H), 8.08 (s, 1H), 11.75 (sbr, 1H), 12.69 (sbr, 1H):LC/MS: m/z 376 (M+1), 378 (M+3)

Example 48

2-(2-Chloro-phenylimino)-5-(4-hydroxy-3-methoxy-benzylidene)-thiazolidin-4-one

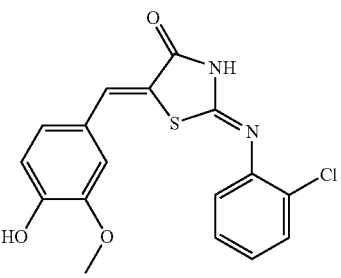

¹H NMR (DMSO-d$_6$) δ 3.75 (s, 3H), 6.88 (m, 2H), 7.15 (t, 1H), 7.19 (t, 1H), 7.36 (t, 1H), 7.53 (d, 1H), 7.58 (s, 1H), 9.80 (sbr, 1H), 12.30 (sbr, 1H): LC/MS: m/z 361 (M+1), 363 (M+3)

Example 49

2-(2-Chloro-phenylimino)-5-(4-hydroxy-2-methoxy-benzylidene)-thiazolidin-4-one

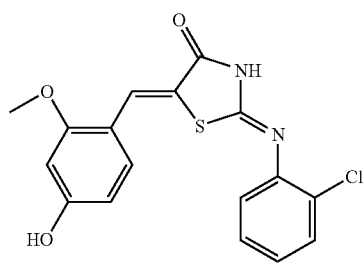

¹H NMR (DMSO-d$_6$) δ 3.81 (s, 3H), 6.47 (m, 2H), 7.10 (m, 2H), 7.19 (t, 1H), 7.35 (t, 1H), 7.53 (d, 1H), 7.83 (s, 1H), 10.30 (sbr, 1H), 12.21 (sbr, 1H) 360

Example 50

2-(2-Chloro-phenylimino)-5-(4-hydroxy-benzylidene)-thiazolidin-4-one

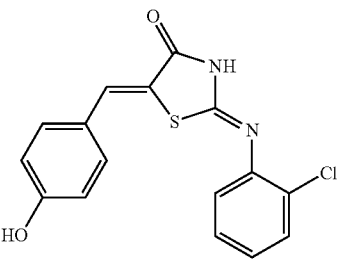

¹H NMR (DMSO-d$_6$) δ 6.86 (d, 2H), 7.13 (d, 1H), 7.20 (t, 1H), 7.34 (d, 2H), 7.36 (m, 1H), 7.53 (d, 1H), 7.58 (s, 1H), 10.20 (sbr, 1H), 12.48 (sbr, 1H): LC/MS: m/z 331 (M+1), 333 (M+3)

Example 51

2-(2-Chloro-phenylimino)-5-(4-methoxy-benzylidene)-thiazolidin-4-one

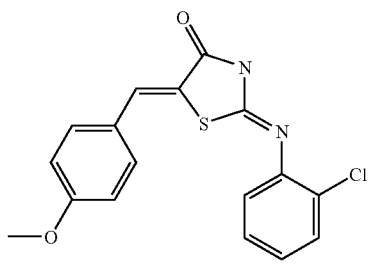

¹H NMR (DMSO-d$_6$) δ 3.78 (s, 3H), 7.05 (d, 2H), 71-6 (m, 1H), 7.21 (t, 1H), 7.37 (t, 1H), 7.46 (d, 2H), 7.54 (d, 1H), 7.63 (s, 1H), 12.54 (sbr, 1H): LC/MS: m/z 345 (M+1), 347 (M+3)

Example 52

5-(3-Chloro-4-hydroxy-benzylidene)-2-(2-chloro-phenylimino)-thiazolidin-4-one

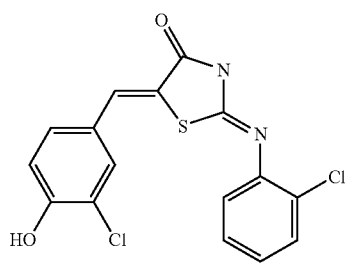

¹H NMR (DMSO-d$_6$) δ 7.06 (d, 1H), 71-6 (d, 1H), 7.21 (t, 1H), 7.28 (d, 1H), 7.37 (t, 1H), 7.55 (m, 3H), 11.02 (sbr, 1H), 12.0 (sbr, 1H): LC/MS: m/z 365 (M+1), 367 (M+3)

Example 53

2-(2-Chloro-phenylimino)-5-(3-fluoro-4-methoxy-benzylidene)-thiazolidin-4-one

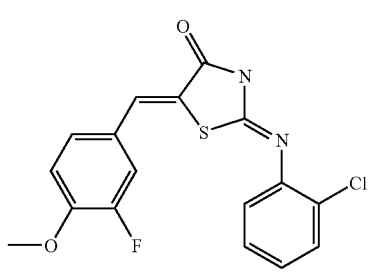

¹H NMR (DMSO-d₆) δ 7.13 (d, 1H), 7.19 (t, 1H), 7.28 (m, 2H), 7.36 (t, 1H), 7.40 (d, 1H), 7.53 (d, 1H), 7.58 (s, 1H), 12.59 (sbr, 1H) 362

Example 54

2-(2,6-Dichloro-phenylimino)-5-(3-fluoro-4-hydroxy-benzylidene)-thiazolidin-4-one

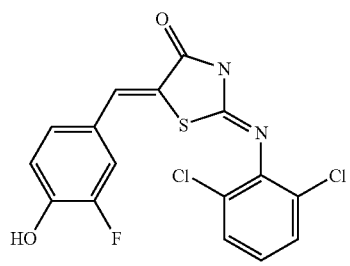

¹H NMR (DMSO-d₆) δ 7.03 (t, 1H), 7.12 (mbr, 2H), 7.30 (d, 1H), 7.50 (mbr, 3H), 12.08 (sbr, 1H): LC/MS: m/z 383 (M+1), 385 (M+3)

Example 55

2-(2-Chloro-phenylimino)-5-(3-fluoro-4-hydroxy-benzylidene)-thiazolidin-4-one

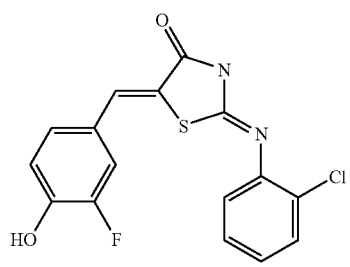

¹H NMR (DMSO-d₆) δ 7.05 (t, 1H), 71-6 (d, 1H), 7.21 (t, 1H), 7.37 (m, 2H), 7.54 (d, 1H), 7.58 (s, 1H), 10.67 (sbr, 1H), 12.11 (sbr, 1H): LC/MS: m/z 349 (M+1), 351 (M+3)

Example 56

2-(2-Chloro-5-fluoro-phenylimino)-5-(3-fluoro-4-hydroxy-benzylidene)-thiazolidin-4-one

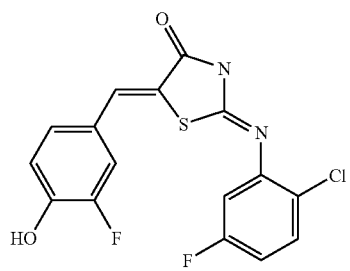

¹H NMR (DMSO-d₆) δ 7.04-7.13 (m, 3H), 7.17 (d, 1H), 7.39 (d, 1H), 7.60 (m, 2H), 10.69 (sbr, 1H), 12.00 (sbr, 1H): LC/MS: m/z 367 (M+1), 369 (M+3)

Example 57

5-(3-Fluoro-4-hydroxy-benzylidene)-2-o-tolylimino-thiazolidin-4-one

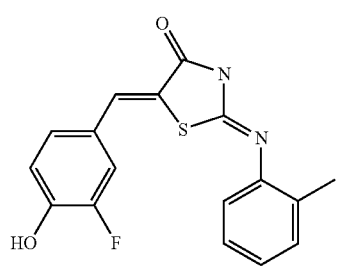

¹H NMR (DMSO-d₆) δ 21-6 (s, 3H), 6.94 (d, 1H), 7.04 (t, 1H), 7.12 (m, 2H), 7.23 (t, 1H), 7.28 (d, 1H), 7.33 (d, 1H), 7.54 (s, 1H), 10.66 (sbr, 1H), 12.12 (sbr, 1H):LC/MS:m/z 329 (M+1)

Example 58

2-(2-Chloro-phenylimino)-5-quinolin-6-ylmethylene-thiazolidin-4-one

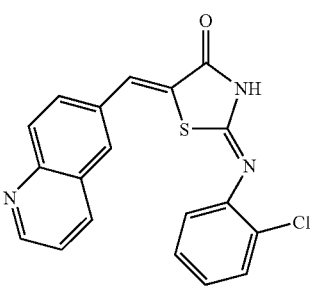

¹H NMR (400 MHz, DMSO-d₆) ppm 7.17-7.25 (m, 2H), 7.39 (m, 1H), 7.57 (m, 2H), 7.84 (m, 1H), 7.86 (s, 1H), 8.08 (d, 1H, J=8.8 Hz), 81-6 (s, 1H), 8.45 (d, 1H, J=7.8 Hz), 8.93 (m, 1H). LC/MS: m/z 366 (M+1)+, 364 (M−1)−.

Example 59

5-Quinolin-6-ylmethylene-2-(2,4,6-trimethyl-phenylimino)-thiazolidin-4-one

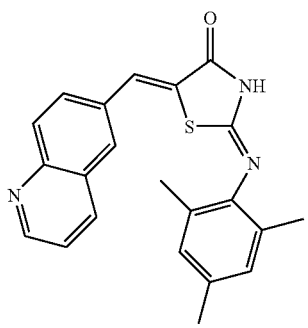

1H NMR (400 MHz, DMSO-d$_6$) ppm 2.15 (s, 6H), 2.27 (s, 3H), 6.95 (s, 2H), 7.56 (m, 1H), 7.81 (m, 2H), 8.07 (d, 1H, J=8.8 Hz), 8.11 (s, 1H), 8.42 (d, 1H, J=8.4 Hz), 8.92 (m, 1H). LC/MS: m/z 374 (M+1)+, 372 (M−1)−.

Example 60

5-Quinolin-6-ylmethylene-2-o-tolylimino-thiazolidin-4-one

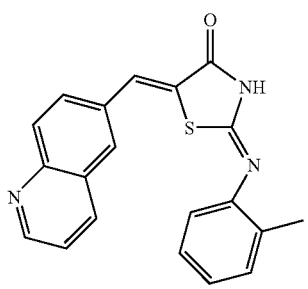

1H NMR (400 MHz, DMSO-d$_6$) ppm 2.17 (s, 3H), 6.98 (m, 1H), 71-6 (m, 1H), 7.22-7.31 (m, 2H), 7.56 (m, 1H), 7.81 (s, 1H), 7.83 (m, 1H), 8.07 (d, 1H, J=8.8 Hz), 8.12 (s, 1H), 8.42 (d, 1H, J=7.6 Hz), 8.92 (m, 1H), 12.47 (m, 1H). LC/MS: m/z 346 (M+1)+, 344 (M−1)−.

Example 61

2-(2-Methoxy-phenylimino)-5-quinolin-6-ylmethylene-thiazolidin-4-one

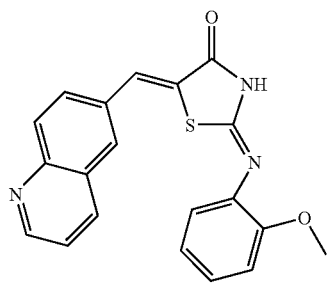

A mixture of E, Z-isomers (ratio=3.0/1.0)

1H NMR (400 MHz, DMSO-d$_6$) ppm 3.78 (s, 2.25H), 3.90 (s, 0.75H), 6.97-7.28 (m, 3H), 7.56 (m, 0.75H), 7.62 (m, 0.25H), 7.81-7.86 (m, 2H), 7.94-8.24 (m, 3H), 8.42-8.51 (m, 1H), 8.92 (m, 0.75H), 8.96 (m, 0.25H), 12.44 (m, 1H). LC/MS: m/z 362 (M+1)+, 360 (M−1)−.

Example 62

5-(2,3-Dihydro-benzofuran-5-ylmethylene)-2-(2-dimethylamino-ethylamino)-thiazol-4-one

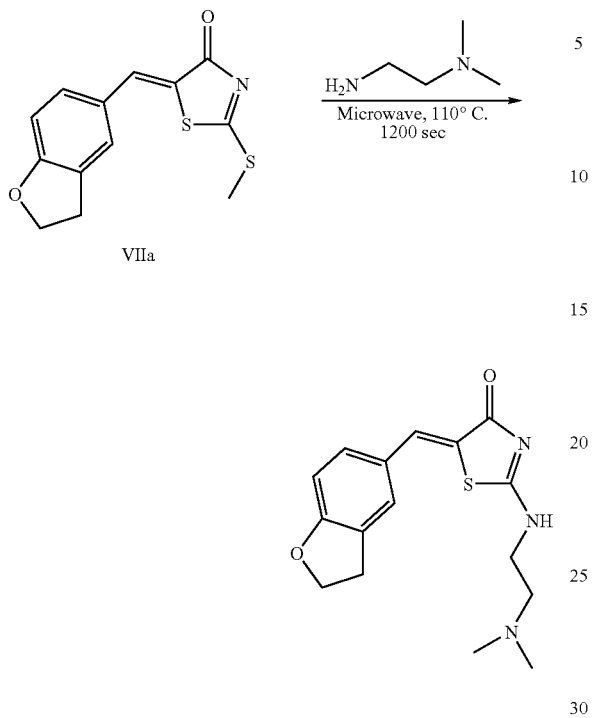

A mixture of aldehyde of formula Va (10 mmol), Rhodanine VIa (10 mmol), sodium acetate (30 mmol), and 10 mL of acetic acid was heated at 110 C.° for 48 h. The reaction mixture was cooled to room temperature and filtered to collect the precipitate formed. The precipitate was washed with acetic acid (1 mL), methanol (1 mL) and dried in vaccuo to give compound VIIa 3.9 g (14.81 mmol).

To room a temperature suspension of VIIa (14.81 mmol) in 100 mL ethanol was added Hunig's base (5.2 mL, 29.85 mmol) followed by iodomethane (4.6 mL, 73.9 mmol). After stirring the resultant suspension at room temperature for 3.5 h, the precipitate was filtered and washed with water to afford compound VIIIa 3.12 g (11.25 mmol) as a first crop. After evaporating the filtrate, to the residue was added methanol (10 mL) and water (10 mL), and the resultant mixture was subjected to sonication for 1 min. The process yielded the second crop which was filtered. 0.8 g (2.89 mmol).

To a mixture of VIIIa (0.3 mmol) and MS4A (molecular sieve 4 Angstrom powder) (250 mg) was added dimethylaminoethylamine (0.45 mmol) and ethanol (1 mL, dehydrated). The mixture was heated by microwave (SmithSynthesizer-Personal Chemistry) at 110 C.° for 1200 seconds. The corresponding product was obtained in 65% yield after purification on SCX column.

$^1$H NMR (400 MHz, DMSO-$d_6$) ppm 2.18 (s, 6H), 2.44 (t, 2H, J=6.6 Hz), 3.24 (t, 2H, J=8.6 Hz), 3.58 (t, 2H, J=6.6 Hz), 4.60 (t, 2H, J=8.6 Hz), 6.90 (d, 1H, J=8.3 Hz), 7.30-7.48 (m, 3H). LC/MS: m/z 318 (M+1)+, 316 (M−1)−.

Example 63-72 compounds were made according to the process B, analogous to the method described in Example 62.

Example 63

Benzoic acid N'-(4-oxo-5-quinolin-6-ylmethylene-4,5-dihydro-thiazol-2-yl)-hydrazide

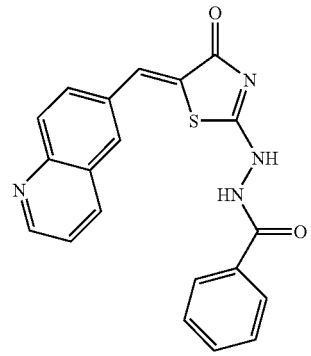

1H NMR (400 MHz, DMSO-$d_6$) ppm 7.49-7.63 (m, 4H), 7.84 (s, 1H), 7.91-7.97 (m, 3H), 8.12 (d, 1H, J=8.8 Hz), 8.23 (d, 1H, J=2.0 Hz), 8.48 (d, 1H, J=7.8 Hz), 8.95 (m, 1H), 11.17 (s, 1H), 12.63 (br, 1H). LC/MS: m/z 375 (M+1)+, 373 (M−1)−.

Example 64

2-(2-Dimethylamino-ethylimino)-5-quinolin-6-ylmethylene-thiazolidin-4-one

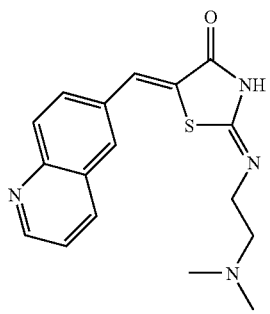

1H NMR (400 MHz, CD$_3$OD) ppm 2.80 (s, 6H), 3.24 (t, 2H, J=6.0 Hz), 3.94 (t, 2H, J=6.0 Hz), 7.57 (m, 1H), 7.88-7.91 (m, 2H), 8.04-8.08 (m, 2H), 8.37-8.45 (m, 2H), 8.86 (dd, 1H, J=1.8, 4.6 Hz). LC/MS: m/z 327 (M+1)+, 325 (M−1)−.

Example 65

5-(2,3-Dihydro-benzofuran-5-ylmethylene)-2-(piperidin-1-ylamino)-thiazol-4-one

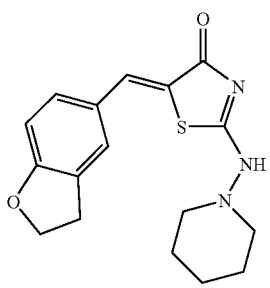

1H NMR (400 MHz, DMSO-d$_6$) ppm 1-60 (br, 2H), 1.63 (m, 4H), 2.27 (m, 4H), 3.26 (t, 2H, J=8.6 Hz), 4.61 (t, 2H, J=8.6 Hz), 6.93 (d, 1H, J=8.4 Hz), 7.37 (dd, 1H, J=1.8, 8.4 Hz), 7.47 (s, 1H), 7.51 (s, 1H), 11.68 (br, 1H). LC/MS: m/z 330 (M+1)+, 328 (M−1)−.

Example 66

2-Benzylamino-5-(2,3-dihydro-benzofuran-5-ylmethylene)-thiazol-4-one

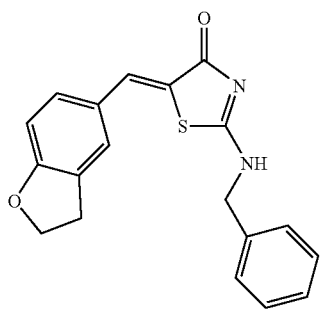

1H NMR (400 MHz, DMSO-d$_6$) ppm 3.25 (t, 2H, J=8.6 Hz), 4.60 (t, 2H, J=8.6 Hz), 4.73 (s, 2H), 6.92 (d, 1H, J=8.4 Hz), 7.29-7.57 (m, 8H), 9.97 (br, 1H). LC/MS: m/z 337 (M+1)+, 335 (M−1)−.

Example 67

2-(4-tert-Butyl-thiazol-2-ylamino)-5-(2,3-dihydro-benzofuran-5-ylmethylene)-thiazol-4-one

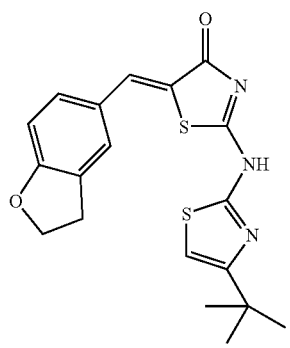

1H NMR (400 MHz, DMSO-d$_6$) ppm 1.35 (s, 9H), 3.24 (t, 2H, J=8.6 Hz), 4.64 (t, 2H, J=8.6 Hz), 6.93 (d, 1H, J=8.3 Hz), 7.02 (s, 1H), 7.46 (dd, 1H, J=1.8, 8.3 Hz), 7.57 (br, 1H), 7.65 (s, 1H), 12.53 (s, 1H). LC/MS: m/z 386 (M+1)+, 384 (M−1)−.

Example 68

4-{[5-(2,3-Dihydro-benzofuran-5-ylmethylene)-4-oxo-4,5-dihydro-thiazol-2-ylamino]-methyl}-benzenesulfonamide

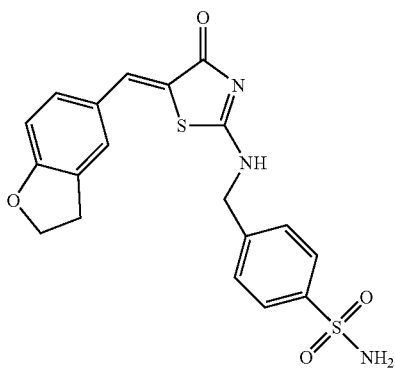

Example 69

5-(2,3-Dihydro-benzofuran-5-ylmethylene)-2-(3-dimethylamino-propylamino)-thiazol-4-one

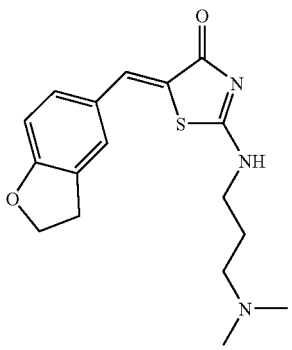

1H NMR (400 MHz, DMSO-d$_6$) ppm 1.74 (m, 2H), 2.13 (s, 6H), 2.25 (t, 2H, J=6.8 Hz), 3.24 (t, 2H, J=8.6 Hz), 3.51 (t, 2H, J=6.8 Hz), 4.61 (t, 2H, J=8.6 Hz), 6.91 (d, 1H, J=8.3 Hz), 7.57-7.52 (m, 3H). LC/MS: m/z 332 (M+1)+, 330 (M−1)−.

Example 70

5-(2,3-Dihydro-benzofuran-5-ylmethylene)-2-(3-imidazol-1-yl-propylamino)-thiazol-4-one

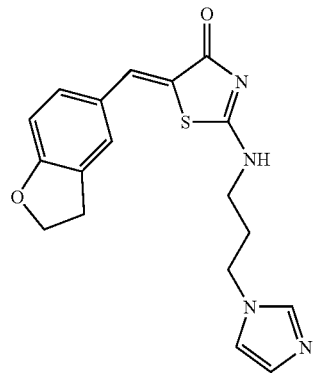

1H NMR (400 MHz, DMSO-d₆) ppm 2.04 (m, 2H), 3.25 (t, 2H, J=8.8 Hz), 3.45 (t, 2H, J=7.0 Hz), 4.04 (t, 2H, J=7.0 Hz), 4.61 (t, 2H, J=8.8 Hz), 6.91 (s, 1H), 6.92 (d, 1H, J=8.6 Hz), 7.22 (t, 1H, J=1.3 Hz), 7.34 (dd, 1H, J=1.5, 8.3 Hz), 7.43 (s, 1H), 7.55 (s, 1H), 7.66 (m, 1H), 9.57 (br, 1H). LC/MS: m/z 355 (M+1)+, 353 (M−1)−.

Example 71

Phenyl-carbamic acid N'-[5-(2,3-dihydro-benzofuran-5-ylmethylene)-4-oxo-4,5-dihydro-thiazol-2-yl]-hydrazide

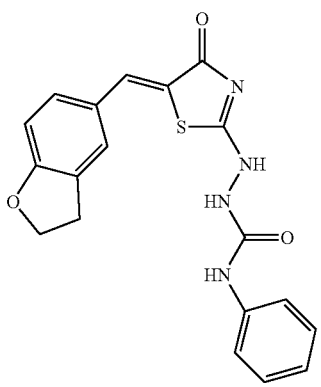

1H NMR (400 MHz, DMSO-d₆) ppm 3.26 (t, 2H, J=8.8 Hz), 4.62 (t, 2H, J=8.8 Hz), 6.93-7.01 (m, 2H), 7.24-7.62 (m, 6H), 9.17 (s, 1H). LC/MS: m/z 381 (M+1)+, 379 (M−1)−.

Example 72

Benzoic acid N'-[5-(2,3-dihydro-benzofuran-5-ylmethylene)-4-oxo-4,5-dihydro-thiazol-2-yl]-hydrazide

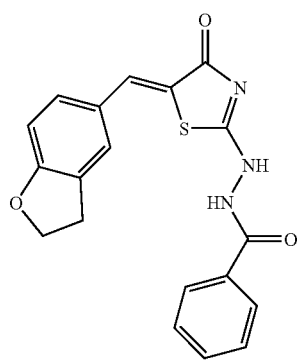

1H NMR (400 MHz, DMSO-d₆) ppm 3.23 (t, 2H, J=8.6 Hz), 4.60 (t, 2H, J=8.6 Hz), 6.91 (d, 1H, J=8.3 Hz), 7.37 (dd, 1H, J=1.5, 8.3 Hz), 7.47-7.61 (m, 5H), 7.90 (d, 2H, J=7.3 Hz), 11.08 (s, 1H), 12.49 (br, 1H). LC/MS: m/z 355 (M+1)+, 353 (M−1)−.

Example 73

5-Benzo[1,2,5]thiadiazol-5-ylmethylene-2-(2,3,4-trifluoro-phenylamino)-thiazol-4-one

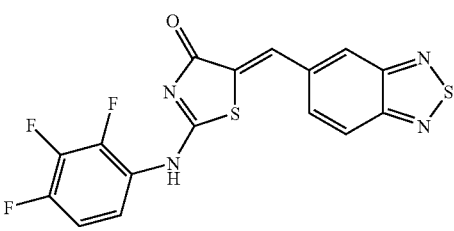

¹H NMR (DMSO-d₆) δ 7.07 (m, 1H), 7.37 (q, 1H), 7.86 (dd, 1H), 7.90 (s, 1H), 8.17 (d, 1H), 8.25 (d, 1H), 12.84 (s, 2H): LC/MS: m/z 393(M+1).

Example 74

5-Benzo[1,2,5]oxadiazol-5-ylmethylene-2-(2-nitro-phenylamino)-thiazol-4-one

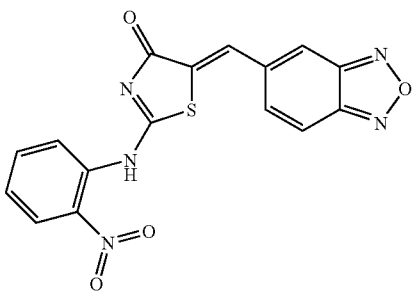

¹H NMR (DMSO-d₆) δ 7.33 (d, 1H), 7.40 (t, 1H), 7.73 (m, 2H), 7.81 (s, 1H), 8.04 (d, 1H), 8.12 (d, 1H), 8.18 (s, 1H), 12.97 (sbr, 1H): LC/MS: m/z 368 (M+1).

Example 75

2-(2,6-Dichloro-phenylamino)-5-(4-[1,2,4]triazol-1-yl-benzylidene)-thiazol-4-one

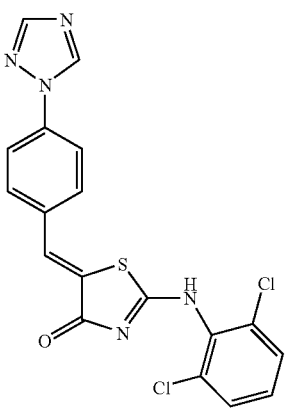

¹H NMR (DMSO-d₆) δ 7.23 (t, 1H), 7.57 (d, 1H), 7.69 (d, 1H), 7.78 (s, 1H), 7.97 (d, 1H), 8.27 (s, 1H), 9.34 (s, 1H), 12.99 (sbr, 1H): LC/MS: m/z 416 (M+1).

Example 76

2-(2,6-Dichloro-phenylamino)-5-(1H-pyrrolo[2,3-b]pyridin-2-ylmethylene)-thiazol-4-one

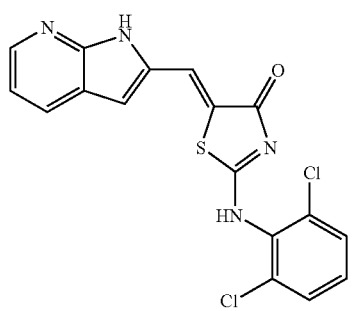

¹H NMR (DMSO-d₆) δ 7.20-7.24 (m, 2H), 7.56 (d, 2H), 7.68 (s, 1H), 7.97 (s, 1H), 8.34 (m, 2H), 12.53 (s, 1H), 12.65 (sbr, 1H): LC/MS: m/z 389 (M+1), 391 (M+3)

Example 77

5-Benzo[1,2,5]thiadiazol-5-ylmethylene-2-(2,6-dichloro-phenylamino)-thiazol-4-one

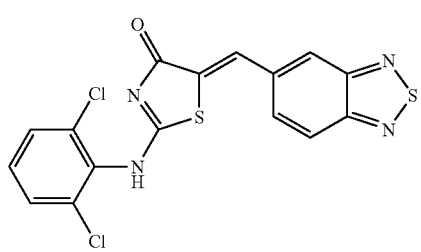

¹H NMR (DMSO-d₆) δ 7.24 (t, 1H), 7.57 (d, 2H), 7.81 (d, 1H), 7.95 (s, 1H), 8.16 (d, 1H), 8.25 (s, 1H), 13.10 (sbr, 1H): LC/MS: m/z 407 (M+1), 409 (M+3).

Example 78

5-[2-(2-Methoxy-6-methyl-phenylamino)-4-oxo-4H-thiazol-5-ylidenemethyl]-1H-pyridin-2-one

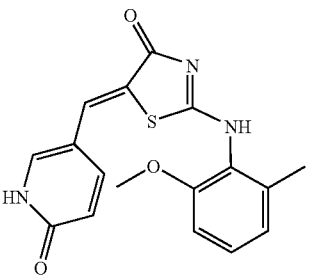

¹H NMR (DMSO-d₆) δ 2.09 (s, 1H), 3.72 (s, 3H), 6.40 (d, 1H), 6.86 (d, 1H), 6.92 (d, 1H), 7.08 (t, 1H), 7.42 (s, 1H), 7.45 (dd, 1H), 7.78 (s, 1H), 12.04 (sbr, 1H): LC/MS: m/z 342 (M+1)

Example 79

5-Benzo[1,2,5]thiadiazol-5-ylmethylene-2-(2-nitro-phenylamino)-thiazol-4-one

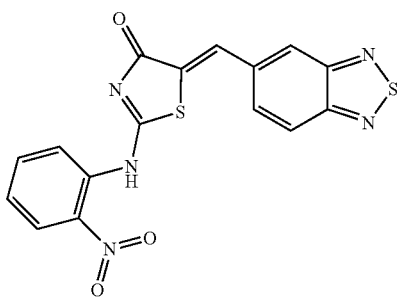

¹H NMR (DMSO-d₆) δ 7.34 (d, 1H), 7.40 (mbr, 1H), 7.73 (t, 1H), 7.86 (d, 1H), 7.90 (sbr, 1H), 8.03 (d, 1H), 8.16 (d, 1H), 8.24 (d, 1H), 11.98 (sbr, 1H): LC/MS: m/z 384 (M+1).

Example 80

2-(2-Bromo-6-fluoro-phenylamino)-5-quinolin-6-ylmethylene-thiazol-4-one

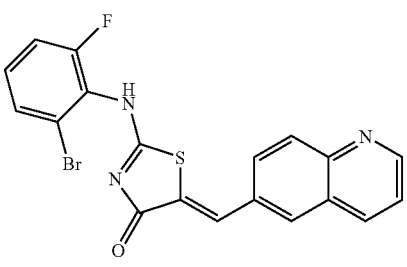

¹H NMR (DMSO-d₆) δ 7.18 (q, 1H), 7.39 (t, 1H), 7.55 (t, 1H), 7.58 (s, 1H), 7.85 (d, 1H), 7.86 (s, 1H), 8.07 (d, 1H), 81-6 (s, 1H), 8.46 (d, 1H), 8.93 (d, 1H), 12.98 (sbr, 1H): LC/MS: m/z 428 (M), 430 (M+2).

Example 81

2-(2-Methoxy-6-methyl-phenylamino)-5-quinolin-6-ylmethylene-thiazol-4-one

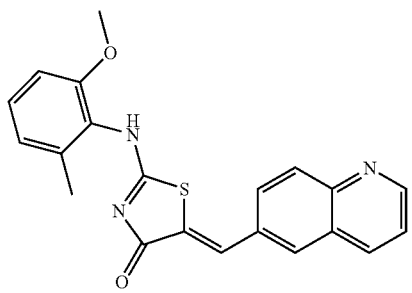

¹H NMR (DMSO-d₆) δ 2.10 (s, 3H), 3.72 (s, 3H), 6.87 (d, 1H), 6.92 (d, 1H), 7.07 (t, 1H), 7.54 (dd, 1H), 7.69 (s, 1H), 7.81 (d, 1H), 8.04 (d, 1H), 8.06 (s, 1H), 8.40 (d, 1H), 8.90 (d, 1H), 12.02 (sbr, 1H): LC/MS: m/z 376 (M+1).

Example 82

5-Quinolin-6-ylmethylene-2-(2,3,4-trifluoro-phenylamino)-thiazol-4-one

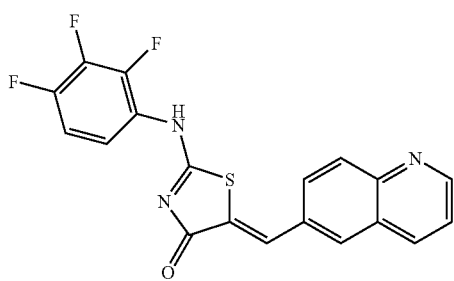

¹H NMR (DMSO-d₆) δ 7.06 (m, 1H), 7.37 (q, 1H), 7.58 (q, 1H), 7.84 (s, 1H), 7.88 (d, 1H), 8.08 (d, 1H), 8.15 (s, 1H), 8.46 (d, 1H), 8.93 (m, 1H), 11.99 (sbr, 1H):LC/MS:m/z 386 (M+1).

Example 83

2-(2,6-Dichloro-phenylamino)-5-(2-oxo-2H-chromen-6-ylmethylene)-thiazol-4-one

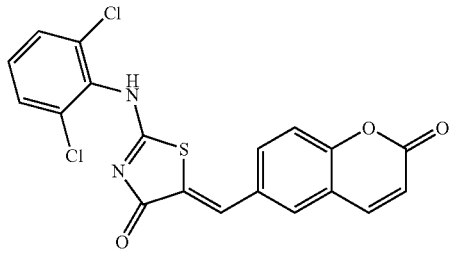

¹H NMR (DMSO-d₆) δ 6.52 (d, 1H), 7.23 (t, 1H), 7.49 (d, 1H), 7.56 (d, 2H), 7.73 (d, 1H), 7.77 (s, 1H), 7.85 (s, 1H), 8.15 (d, 1H), 12.99 (sbr, 1H): LC/MS: m/z 417 (M+1), 419 (M+3).

Example 84

2-(2-Bromo-phenylamino)-5-(5-pyridin-2-yl-thiophen-2-ylmethylene)-thiazol-4-one

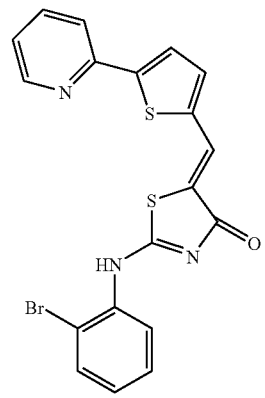

¹H NMR (DMSO-d₆) δ 7.17 (t, 2H), 7.32 (dd, 1H), 7.46 (t, 1H), 7.63 (d, 1H), 7.72 (d, 1H), 7.86 (t, 1H), 7.91 (m, 2H), 7.99 (d, 1H), 8.54 (d, 1H), 12.65 (sbr, 1H):LC/MS:m/z 442 (M), 444(M+2).

Example 85

2-(2-Bromo-phenylamino)-5-(1-oxy-pyridin-4-ylmethylene)-thiazol-4-one

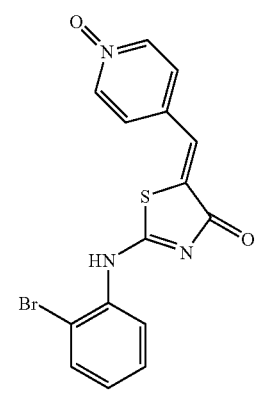

¹H NMR (DMSO-d₆) δ 7.14 (t, 2H), 7.42 (t, 1H), 7.49 (d, 2H), 7.63 (s, 1H), 7.70 (d, 1H), 8.22 (d, 2H), 12.82 (sbr, 1H): LC/MS: m/z 376 (M), 378 (M+2).

Example 86

2-(2-Bromo-phenylamino)-5-(3-p-tolyl-benzo[c]isoxazol-5-ylmethylene)-thiazol-4-one

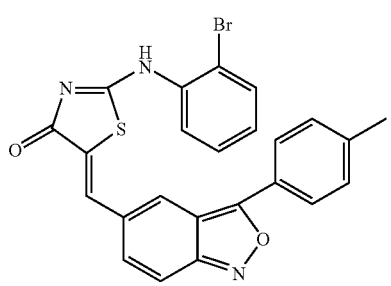

¹H NMR (DMSO-d₆) δ 2.44 (t, 3H), 7.15 (m, 2H), 7.42 (m, 3H), 7.51 (d, 1H), 7.72 (t, 2H), 7.81 (s, 1H), 8.02 (d, 2H), 8.45 (s, 1H), 12.73 (sbr, 1H): LC/MS: m/z 490 (M), 492 (M+2).

Example 87

2-(2-Bromo-phenylamino)-5-(3,4-dihydro-2H-benzo[b][1-6]dioxepin-7-ylmethylene)-thiazol-4-one

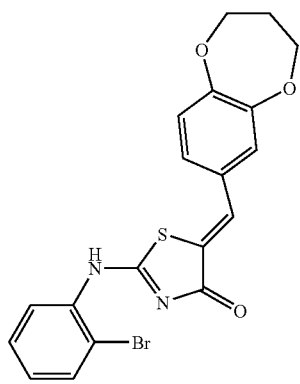

¹H NMR (DMSO-d₆) δ 2.10 (m, 2H), 4.16 (quint, 4H), 7.03 (m, 1H), 7.08-7.15 (m, 4H), 7.42 (t, 1H), 7.57 (s, 1H), 7.70 (d, 1H), 12.59 (sbr, 1H): LC/MS: m/z 431 (M), 433 (M+2).

Example 88

5-Benzo[1,2,5]oxadiazol-5-ylmethylene-2-(2-bromo-phenylamino)-thiazol-4-one

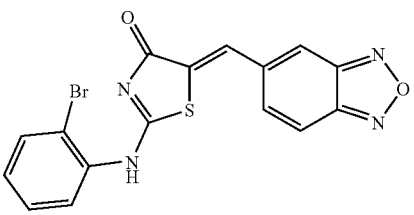

¹H NMR (DMSO-d₆) δ 7.13 (m, 2H), 7.41 (t, 1H), 7.71 (t, 2H), 7.76 (s, 1H), 8.11 (d, 1H), 8.13 (s, 1H), 12.92 (sbr, 1H): LC/MS: m/z 401 (M), 403 (M+2).

Example 89

2-(2,6-Dichloro-phenylamino)-5-(2-methoxy-pyridin-3-ylmethylene)-thiazol-4-one

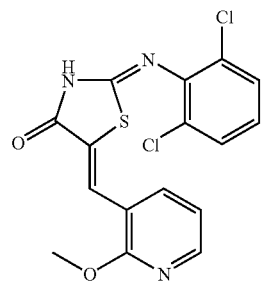

¹H NMR (DMSO-d₆) δ 3.88 (s, 3H), 6.91 (d, 1H), 7.20 (t, 1H), 7.54 (d, 2H), 7.66 (s, 1H), 7.73 (d, 1H), 8.42 (s, 1H), 12.89 (sbr, 1H): LC/MS: m/z 380 (M+1), 382 (M+3).

Example 90

2-(2-Chloro-phenylamino)-5-(6-methoxy-pyridin-3-ylmethylene)-thiazol-4-one

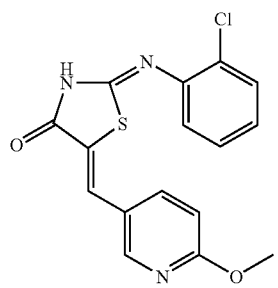

¹H NMR (DMSO-d₆) δ 3.88 (s, 3H), 6.92 (d, 1H), 71-6 (d, 1H), 7.21 (t, 1H), 7.37 (t, 1H), 7.54 (d, 1H), 7.67 (s, 1H), 7.75 (dd, 1H), 8.43 (dd, 1H), 12.66 (sbr, 1H):LC/MS:m/z 346 (M+1), 348 (M+3).

Example 91

2-(2-Chloro-5-trifluoromethyl-phenylamino)-5-quinolin-6-ylmethylene-thiazol-4-one

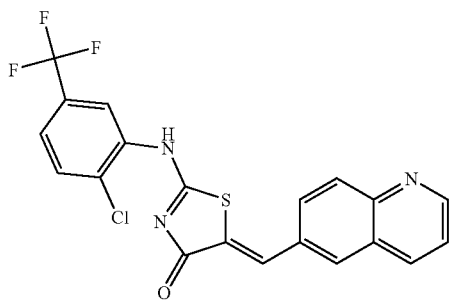

$^1$H NMR (DMSO-d$_6$) δ 7.56 (m, 3H), 7.87 (mbr, 3H), 8.06 (d, 1H), 81-6 (s, 1H), 8.44 (d, 1H), 8.92 (m, 1H), 12.89 (sbr, 1H): LC/MS m/z 434 (M+1), 436 (M+3).

Example 92

2-(2-Bromo-phenylamino)-5-(4-hydroxy-3-methoxy-benzylidene)-thiazol-4-one

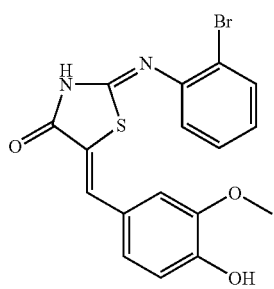

$^1$H NMR (DMSO-d$_6$) δ 3.75 (s, 3H), 6.87 (m, 2H), 7.10 (m, 2H), 7.13 (s, 1H), 7.38 (m, 1H), 7.53 (s, 1H), 7.67 (d, 1H), 9.77 (sbr, 1H): LC/MS m/z 405 (M), 407 (M+2).

Example 93

5-(2,3-Dihydro-benzofuran-5-ylmethylene)-2-(2-methoxy-phenylamino)-thiazol-4-one

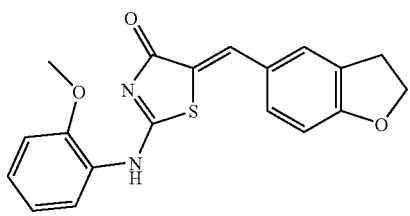

$^1$H NMR (DMSO-d$_6$) δ 3.19 (t, 2H), 3.76 (s, 3H), 4.57 (t, 2H), 6.87 (t, 1H), 6.98 (mbr, 2H), 7.09 (d, 1H), 7.19 (m, 1H), 7.26 (d, 1H), 7.35 (s, 1H), 7.56 (s, 1H), 11.0 (sbr, 1H) LC/MS m/z 353 (M+1).

Example 94

2-(2-Nitro-phenylamino)-5-quinolin-6-ylmethylene-thiazol-4-one

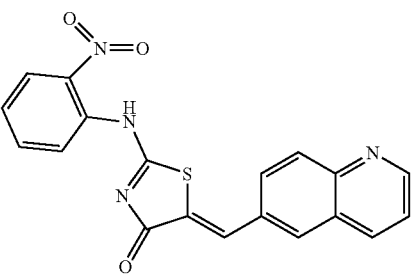

$^1$H NMR (DMSO-d$_6$) δ 7.24 (sbr, 1H), 7.40 (sbr, 1H), 7.55 (dd, 1H), 7.63 (mbr, 2H), 7.89 (m, 2H), 8.06 (d, 1H), 8.11 (d, 1H), 8.43 (d, 1H), 8.91 (dd, 1H):LC/MS m/z 377 (M+1).

Example 95

2-(2-Bromo-phenylamino)-5-(3,4-diamino-benzylidene)-thiazol4-one

Scheme C

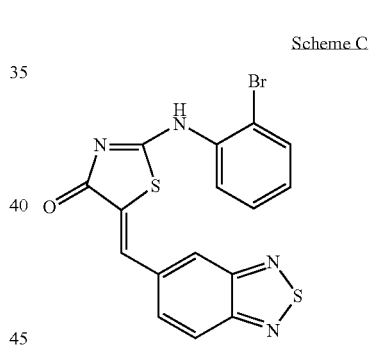

Example 44

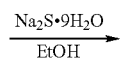

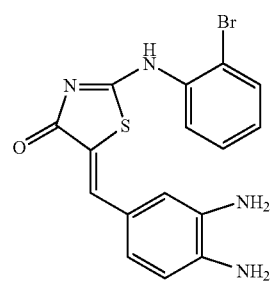

Example 95

A mixture of the product of compound of Example 44 (380 mg) and Na$_2$S-9H$_2$O (600 mg) in ethanol was irradiated by a microwave reactor at 120 C.° for 5 hours. The mixture was poured onto aq.NH$_4$Cl and the formed orange precipitate was filtrated. Washing with H$_2$O and subsequent desiccation gave compound the title compound.

$^1$H NMR (DMSO-d$_6$) δ 4.68 (sbr, 2H), 5.30 (s, 2H), 6.44-6.55 (m, 3H), 7.04 (m, 2H), 7.29 (s, 1H), 7.33 (t, 1H), 7.61 (d, 1H): LC/MS: m/z 389 (M), 391 (M+2).
Example 96
5-[2-(2-Chloro-phenylimino)-4-oxo-thiazolidin-5-ylidenemethyl]-1-methyl-1H-pyridin-2-one
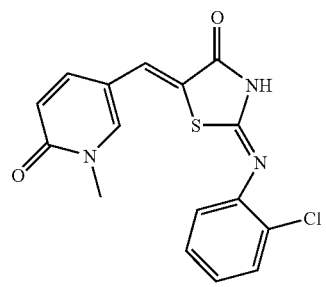
$^1$H NMR (400 MHz, DMSO-d$_6$) ppm 3.45 (s, 3H), 6.48 (d, 1H, J=9.6 Hz), 7.13 (d, 1H, J=7.8 Hz), 7.19 (m, 1H), 7.36 (m, 1H), 7.43 (s, 1H), 7.47 (dd, 1H, J=2.6, 9.6 Hz), 7.53 (d, 1H, J=8.1 Hz), 8.23 (d, 1H, J=2.8 Hz), 12.15 (br, 1H). LC/MS: m/z 346 (M+1)+, 344 (M−1)−.
Synthesis of Compounds of Example 97-99
Scheme D
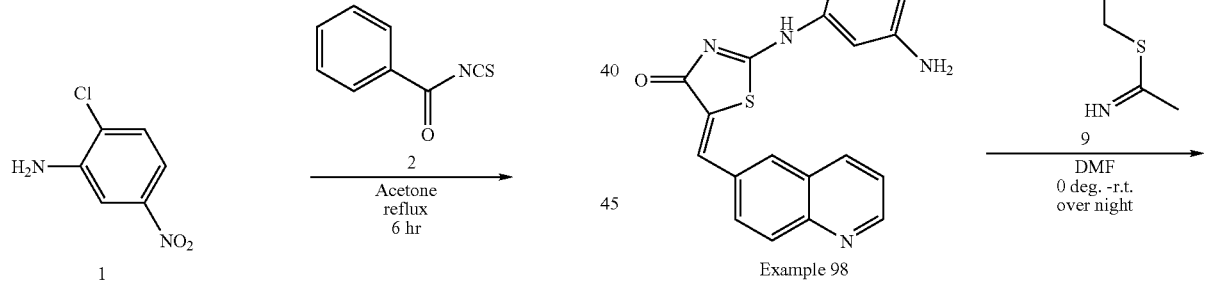
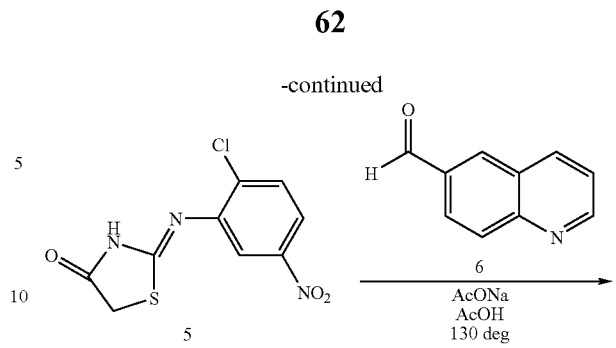
Example 97
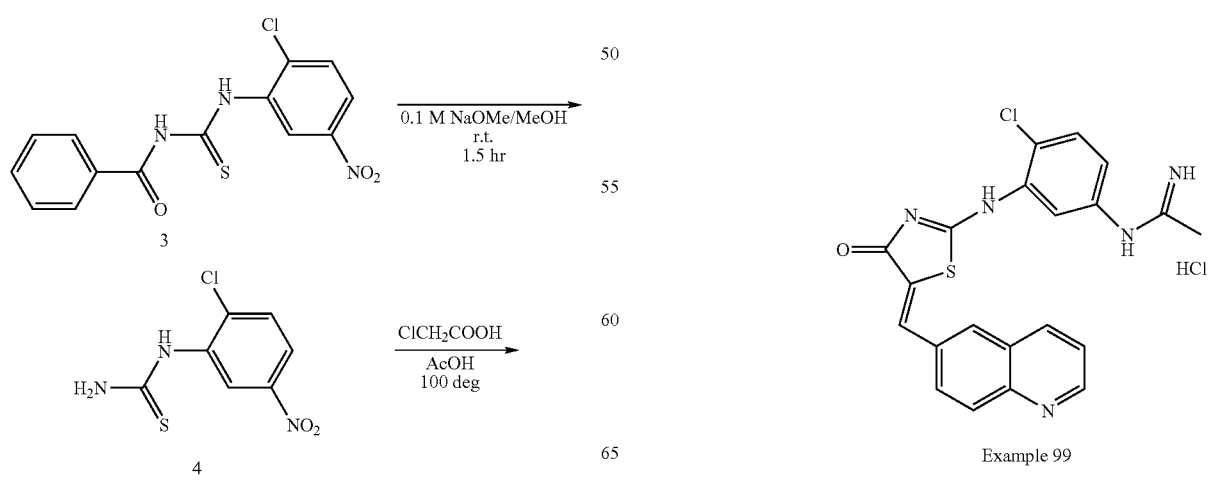
Example 98
Example 99

Example 97

2-(2-Chloro-5-nitro-phenylamino)-5-quinolin-6-ylmethylene-thiazol4-one

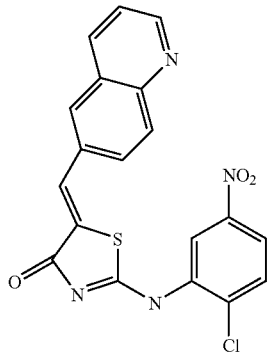

A mixture of 2-chloro-5-nitroaniline 1 (5.2 g, 30 mmol) and benzoyl isothiacyanate 2 (5.4 g, 33 mmol) in 40 ml of acetone was refluxed for 6 hours and then cooled and left to stand at room temperature. The separated crystalline solid was collected by filtration and washed with acetone and dried in vacuo to give benzoyl thiourea 3 (9.4 g, 28 mmol). 9.0 g (26.8 mmol) of Benzoyl thiourea 3 was treated with 600 ml of 0.1M sodium methoxide solution. The yellow-orange solution formed was left to stand at room temperature overnight, then neutralized with methanolic hydrogen chloride to pH 7. The resulting solution was treated with 100 ml of water and the mixture was concentrated to 200 ml by vacuum distillation. The separated yellow crystalline solid was collected by filtration. After recrystallization from water-acetone (2:1) 2.77 g (11.9 mmol) of thiourea 4 was obtained. A mixture of 4 (2.3 g, 10 mmol) and ClCH$_2$CO$_2$H (1.1 g) in AcOH (20 mL) was heated at 100 C.° for overnight. The mixture was poured onto water and the formed solid was isolated by filtration. It was washed with water to give thiazolidinone 5 (1.65 g, 6.1 mmol). A mixture of 5 (272 mg, 1.0 mmol), aldehyde 6 (157 mg, 1.0 mmol) and AcONa (246 mg, 3.0 mmol) in AcOH (10 mL) was heated to reflux at 130 C.° for 10 days. Generated solid was collected by filtration and washed with AcOH and water, followed by desiccation in vacuo to afford the title product (328 mg, 0.80 mmol). 1H NMR(DMSO-d$_6$) δ 12.95 (s, 1H), 8.94 (m, 1H), 8.45 (d, 1H), 8.16 (s, 1H), 8.09-8.04 (m, 3H), 7.90 (s, 1H), 7.90-7.85 (m, 2H), 7.57 (dd, 1H):LC/MS: m/z 411 (M+1)

Example 98

2-(5-Amino-2-chloro-phenylamino)-5-quinolin-6-ylmethylene-thiazol-4-one

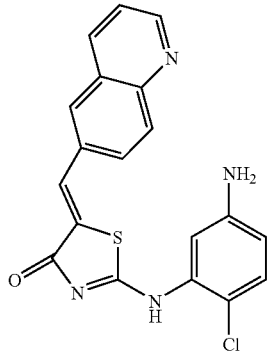

A mixture of 2-(2-chloro-5-nitro-phenylamino)-5-quinolin-6-ylmethylene-thiazol4-one (100 mg, 0.42 mmol) and sodium sulfide nonahydrate (350 mg, 1-66 mmol) in 4 ml of EtOH was heated by microwave (SmithSynthesizer-Personal Chemistry) at 130 for 2 hours. The reaction mixture was cooled to room temperature and concentrated by vacuum distillation, then water was added and neutralized with aqueous ammonium chloride. Generated solid was collected by filtration and washed with water, followed by desiccation in vacuo to afford the title product (33 mg, 0.086 mmol). 1H NMR(DMSO-d$_6$) δ 12.63 (s, 1H) 8.94 (m, 1H) 8.47 (d, 1H) 4.16 (s, 1H) 8.10 (d, 1H) 7.87 (dd, 1H) 7.84 (s, 1H) 7.56 (dd, 1H) 7.12 (d, 1H) 6.40 (d, 1H) 6.38 (s, 1H) 5.37 (s, 2H).:LC/MS: m/z 381 (M+1)

Example 99

N-[4-Chloro-3-(4-oxo-5-quinolin-6-ylmethylene-4,5-dihydro-thiazol-2-ylamino)-phenyl]-acetamidine hydrochloride

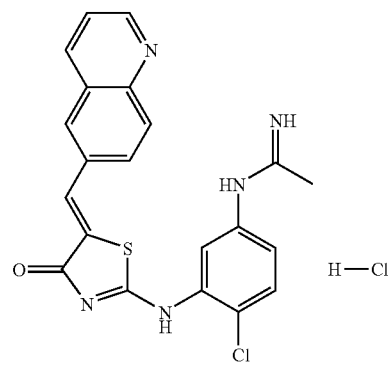

To a stirred, cooled (0 deg.) solution of 2-(5-amino-2-chloro-phenylamino)-5-quinolin-6-ylmethylene-thiazol-4-one (39.7 mg, 0.1 mmol) in DMF (1 ml) was added thioacetimidate hydrochloride 9 (28 mg, 0.11 mmol). The mixture was warmed to room temperature and stirred for over night. DMF was removed by nitrogen gas blowing and resulting oil was dissolved with methanol. Insoluble solid was collected by filtration and washed with methanol, followed by desiccation in vacuo to afford the title (14 mg, 0.031 mmol).

$^1$H NMR(DMSO-d$_6$) δ 12.87 (s, 1H) 11.29 (s, 1H) 9.55 (s, 1H) 8.95 (m, 1H) 8.67 (s, 1H), 8.44 (d, 1H) 8.18 (s, 1H) 8.09 (s, 1H) 7.89 (s, 1H) 7.87 (dd, 1H) 7.74 (d, 1H) 7.60 (dd, 1H) 7.22-7.15 (m, 2H) 2.31 (s, 3H). LC/MS: m/z 422 (M+1)

Note: Thioacetimidate hydrochloride 9 was made according to a procedure in Tetrahedron Letters, Vol. 38, No 2, pp. 179-182, 1997.

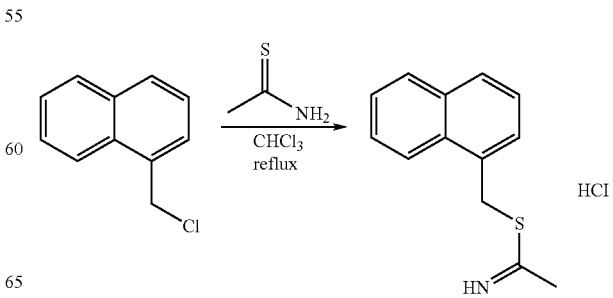

Compounds of Examples 100 to 109 were made analogous to a process describe in Scheme B and Example 62.

Example 100

4-{[4-oxo-5-(6-quinolinylmethylidene)-4,5-dihydro-1,3-thiazol-2-yl]amino}benzamide

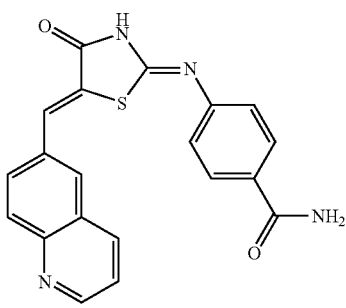

1H NMR (400 MHz, DMSO-$d_6$) ppm 7.11 (d, 1H), 7.48 (d, 1H), 7.55 (m, 1H), 7.82-8.04 (m, 4H), 8.10 (d, 1H), 8.15 (s, 1H), 8.45 (d, 1H), 8.83 (d, 1H), 11.86 (s, 1H). LC/MS: m/z 375 (M+1)+.

Example 101

3-{[4-oxo-5-(6-quinolinylmethylidene)-4,5-dihydro-1,3-thiazol-2-yl]amino}benzenesulfonamide

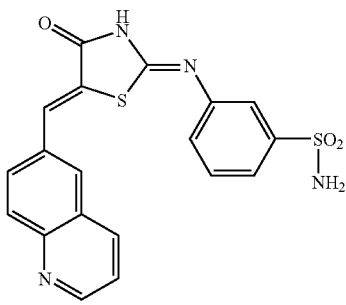

1H NMR (400 MHz, DMSO-$d_6$) ppm 7.40-8.70 (m, 5H), 7.82 (s, 1H), 7.98 (d, 1H), 8.07 (d, 1H), 8.17 (s, 1H), 8.45 (d, 1H), 8.95 (d, 1H). LC/MS: m/z 411 (M+1)+.

Example 102

4-{[4-oxo-5-(6-quinolinylmethylidene)4,5-dihydro-1,3-thiazol-2-yl]amino}-N-2-pyridinylbenzene-sulfonamide

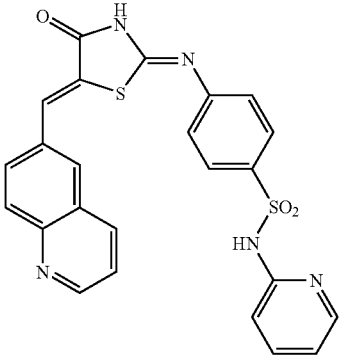

1H NMR (400 MHz, DMSO-$d_6$) ppm 5.95 (s, 1H), 6.54 (d, 2H), 6.89 (m, 1H), 7.05 (d, 1H), 7.20 (m, 1H), 7.50 (d, 2H), 7.63 (m, 1H), 7.7-8.2 (m, 4H), 8.45 (m, 1H)m, 8.95 (m, 1H). LC/MS: m/z 488 (M+1)+.

Example 103

2-({4-[(4-methyl-1-piperazinyl)methyl]phenyl}amino)-5-(6-quinolinylmethylidene)-1,3-thiazol-4(5H)-one

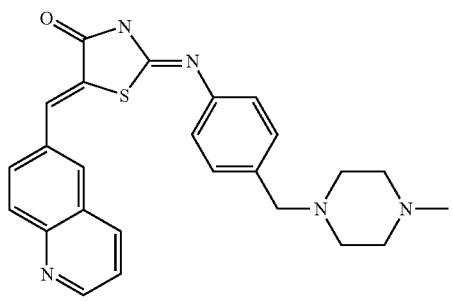

1H NMR (400 MHz, DMSO-$d_6$) ppm 2.38 (s, 3H), 2.65 (m, 4H), 2.86 (m, 4H), 3.68 (s, 2H), 7.06 (d, 1H), 7.38 (d, 2H), 7.60 (m, 1H), 7.76 (d, 1H), 7.80 (s, 1H), 7.91 (s, 1H), 8.00 (d, 2H) 8.25 (m, 1H), 8.45 (m, 1H), 8.95 (m, 1H). LC/MS: m/z 444 (M+1)+.

Example 104

2-({4-[(methylsulfonyl)methyl]phenyl}amino)-5-(6-quinolinylmethylidene)-1,3-thiazol-4(5H)-one

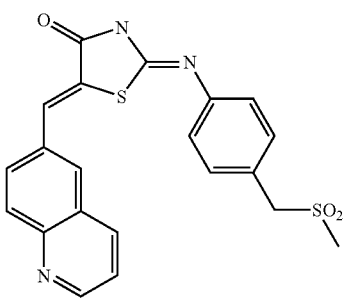

1H NMR (400 MHz, DMSO-d$_6$) ppm 2.92 (s, 3H), 4.52 (s, 2H), 6.53 (d, 1H), 7.01 (d, 1H), 7.10 (m, 1H), 7.48 (d, 2H), 7.62 (m, 1H), 7.83 (d, 2H), 7.95 (s, 1H), 8.47 (d, 1H), 8.95 (m, 1H), 11.80 (s, 1H). LC/MS: m/z 424 (M+1)+.

Example 105

2-({3-[(methylsulfonyl)methyl]phenyl}amino)-5-(6-quinolinylmethylidene)-1,3-thiazol-4(5H)-one

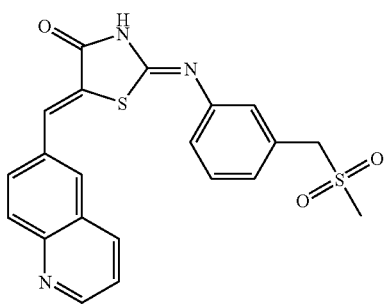

1H NMR (400 MHz, DMSO-d$_6$) ppm 2.96 (s, 3H), 4.58 (s, 2H), 6.53 (d, 1H), 7.12 (m, 1H), 7.35 (d, 1H), 7.50 (m, 1H), 7.61 (m, 1H), 7.85 (s, 1H), 7.95 (d, 1H), 8.05 (s, 1H), 8.11 (s, 1H), 8.47 (d, 1H), 8.95 (m, 1H), 11.80 (s, 1H). LC/MS: m/z 424 (M+1)+.

Example 106

2-{[4-(4-methyl-1-piperazinyl)phenyl]amino}-5-(6-quinolinylmethylidene)-1,3-thiazol-4(5H)-one

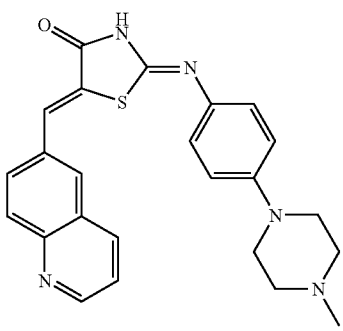

1H NMR (400 MHz, DMSO-d$_6$) ppm 2.25 (d, 4H), 3.28 (d, 4H), 3.35 (s, 3H), 6.98 (d, 2H), 7.00 (d, 1H), 7.53 (m, 1H), 7.62 (d, 2H), 7.85 (s, 1H), 7.95 (d, 1H), 8.21 (s, 1H), 8.47 (d, 1H), 8.95 (m, 1H), 11.80 (s, 1H). LC/MS: m/z 430 (M+1)+.

HPLC retention times in the following Examples were taken by the method: Agilent Eclipse ODS 4.6×250 mm, 1.5 mL/min, 5-95% Water/ACN in 10 min.

Example 107

2-{[2-(3-chlorophenyl)ethyl]amino}-5-(6-quinolinylmethylidene)-1,3-thiazol-4(5H)-one

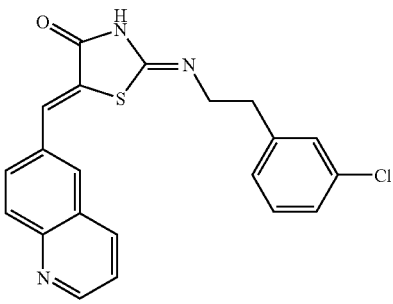

HPLC Rt=4.74 min. LC/MS: m/z 394 (M−1)+, 396 (M+1)+.

Example 108

4-(2-{[4-oxo-5-(6-quinolinylmethylidene)4,5-dihydro-1,3-thiazol-2-yl]amino}ethyl)benzenesulfonamide

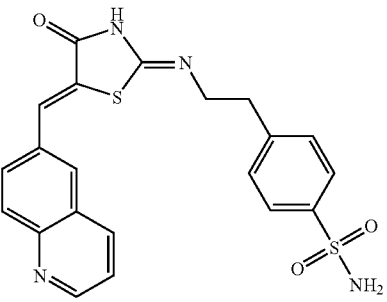

HPLC Rt=3.49 min. LC/MS: m/z 439 (M+1)+.

Example 109

3-{[4-oxo-5-(6-quinolinylmethylidene)-4,5-dihydro-1,3-thiazol-2-yl]amino}benzamide

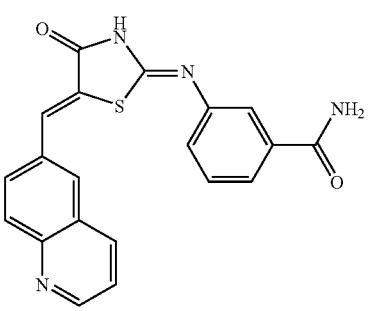

HPLC Rt=3.57 min. LC/MS: m/z 375 (M+1)+.

Compounds in Examples 110-115 were made according to Scheme A with modification that a thiourea of formula III was made according to a method described by Walczynski K et al. in *Il Farmaco* 55 (2000) 569-574 (Scheme E), or by Rasmussen, F. J. et. al. in Synthesis 1988, 456-459.

Scheme E

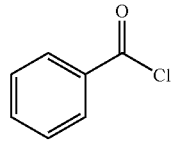 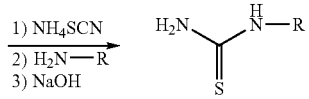

III

Example 110

2-[(2,6-Difluoro-phenylamino)-methylene]-5-quinolin-6-ylmethylene-thiazolidin-4-one

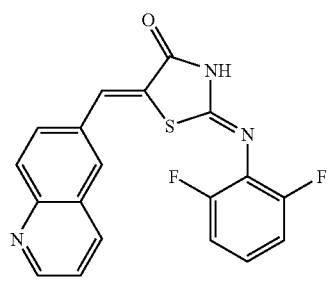

Benzoyl chloride (5.44 g, 38 mmol) was added dropwise to a solution of ammonium thiocyanate (2.55 g, 42.6 mmol) in acetone. Solution was refluxed for 10 minutes at which time a solution of 2,6-difluoro-aniline (5.0 g, 38.8 mmol) in acetone was added dropwise and the solution refluxed for approximately 5 minutes. The solution was then poured into 500 mL of water and a resulting solid precipitated out. The separated crystalline solid was collected by filtration and then heated in a NaOH solution (3 g in 50 mL H$_2$O). The solution was acidified with conc. HCl, then made slightly basic using conc. NH$_4$OH. Crystalline solid was seen and collected to obtain (2,6-difluoro-phenyl)-thiourea. A mixture of the thiourea (5.7 g, 30.3 mmol), AcONa (2.43 g) and ClCH$_2$CO$_2$H (2.86 g) in AcOH (20 mL) was heated to reflux at 130 C.° for four hours. The mixture was poured onto water and the formed solid was isolated by filtration. It was washed with water to give the desired thiazolidinone (a compound of formula IV in which R is 2,6-difluorophenyl) (6.75 g, 29.6 mmol). A mixture of the thiazolidinone (200 mg, 0.8 mmol), 6-formyl quinoline (137 mg, 0.8 mmol) and AcONa (211 mg, 2.4 mmol) in AcOH (10 mL) was heated to reflux at 130 C.° for 2 days. Water was added to the solution and generated a solid that was collected by filtration and washed with water, followed by desiccation in vacuo to afford the title compound as a yellow solid. ES (±) MS m/e=368.0 (M+H). HPLC (rt)–4.53 m

Example 111

2-[(2,6-Difluoro-phenylamino)-methylene]-5-quinolin-6-ylmethylene-thiazolidin-4-one

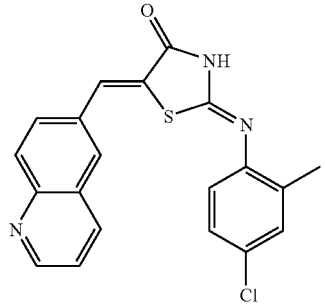

Prepared according to the procedure as in Example 110 above, except using 4-chloro-2-methyl-phenyl)-thiourea (2.00 g, 9.98 mmol; commercially available) as the appropriate thiourea. Title compound was a yellow solid. ES (±) MS m/e=379.8 (M+H). HPLC (rt)–5.19 m

Example 112

[2,4-Dichloro-5-(4-oxo-5-quinolin-6-ylmethylene-thiazolidin-2-ylideneamino)-phenoxy]-acetic acid

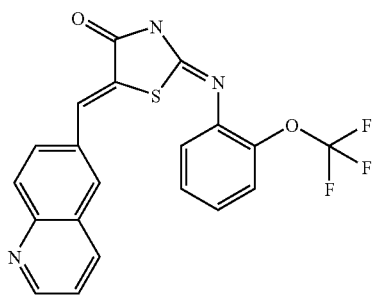

Prepared according to Example 110, except using commercially available benzoyl isothiocyanate instead of generating in situ. A solid precipitate formed and was collected to afford the title compound as a brownish yellow solid. ES (±) MS m/e=416.0 (M+H). HPLC (rt)–5.24 m.

Example 113

2-[2,4-Dichloro-5-(2-methoxy-ethoxy)-phenylimino]-5-quinolin-6-ylmethylene-thiazolidin-4-one

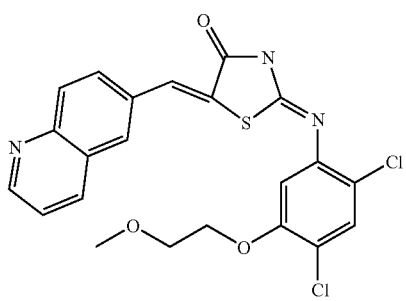

Prepared according to Example 110 above, except using commercially available benzoyl isothiocyanate instead of generating it in situ. A solid precipitate formed and was collected to afford the title compound as a yellow solid. ES (±) MS m/e=474.2 (M+H). HPLC (rt)–5.54 m Example 114

4-Chloro-3-(4-oxo-5-quinolin-6-ylmethylene-thiazolidin-2-ylideneamino)-benzoic acid

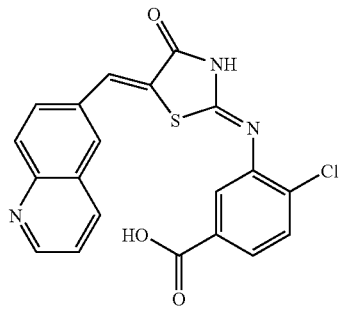

Prepared according to Example 110, except using commercially available benzoyl isothiocyanate instead of generating it in situ. The thiourea did not crystallize so the solution was removed in vacuo and used in thiazolidinone step. The sodium salts were filtered away during this step while the HOAc solution was still hot. The final step yielded a solid precipitate which was collected to afford the title compound as a white solid. ES (±) MS m/e=410.2 (M+H). HPLC (rt)–4.12 m Example 115

[2,4-Dichloro-5-(4-oxo-5-quinolin-6-ylmethylene-thiazolidin-2-ylideneamino)-phenoxy]-acetic acid

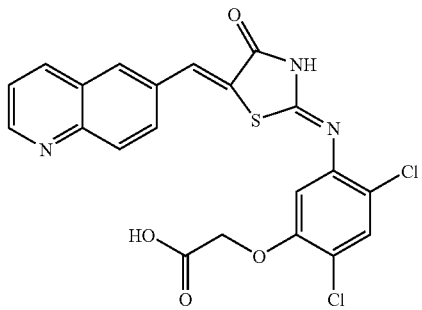

Prepared according to Example 110, except using commercially available benzoyl isothiocyanate instead of generating it in situ. The initial aniline, (5-Amino-2,4-dichloro-phenoxy)-acetic acid ethyl ester, was hydrolyzed to an acid by stirring with NaOH. The thiourea did not crystallize so the solution was removed in vacuo and used in thiazolidinone step. The sodium salts were filtered away during this step while the HOAc solution was still hot. The final step yielded a solid precipitate which was collected to afford the title compound as a white solid. ES (±) MS m/e=474.0 (M+H). HPLC (rt)–4.73 m Biological Methods and Data As demonstrated by the representative compounds of the present invention in Table 1, the compounds of the present invention have valuable pharmacological properties due to their potent ability to inhibit the hYAK3 kinase enzyme.

Substrate phosphorylation assays were carried out as follows:

YAK3 Scintillation Proximity Assays Using Ser164 of Myelin Basic Protein as the Phosphoacceptor The source of Ser164 substrate peptide The biotinylated Ser164, S164A peptide(Biotinyl-LGGRDSRAGS*PMARR—OH) (SEQ ID NO: 1), sequence derived from the C-terminus of bovine myelin basic protein (MBP) with Ser162 substituted as Ala162, was purchased from California Peptide Research Inc. (Napa, Calif.), and its purity was determined by HPLC. Phosphorylation occurs at position 164 (marked S* above). The calculated molecular mass of the peptide was 2166 dalton. Solid sample was dissolved at 10 mM in DMSO, aliquoted, and stored at −20° C. until use.

The source of enzyme:

hYAK3: Glutathione-S-Transferase (GST)-hYak3-His6 containing amino acid residues 124-526 of human YAK3 (SEQ ID NO: 2) (aa 124-526 of SEQ ID NO 2. in U.S. Pat. No. 6,323,318) was purified from baculovirus expression system in Sf9 cells using Glutathione Sepharose 4B column chromatography followed by Ni-NTA-Agarose column chromatography. Purity greater than 65% typically was achieved. Samples, in 50 mM Tris, 150 mM NaCl, 10% glycerol, 0.1% Triton, 250 mM imidazole, 10 mM β-mercapto ethanol, pH 8.0. were stored at −80° C. until use.

Kinase assay of purified hYAK3: Assays were performed in 96 well (Costar, Catalog No. 3789) or 384 well plates (Costar, Catalog No. 3705). Reaction (in 20, 25, or 40 μl volume) mix contained in final concentrations 25 mM Hepes buffer, pH 7.4; 10 mM $MgCl_2$; 10 mM β-mercapto ethanol; 0.0025% Tween-20; 0.001 mM ATP, 0.1 μCi of [γ-$^{33}$P]ATP; purified hYAK3 (7-14 ng/assay; 4 nM final); and 4 μM Ser164 peptide. Compounds, titrated in DMSO, were evaluated at concentrations ranging from 50 μM to 0.5 nM. Final assay concentrations of DMSO did not exceed 5%, resulting in less than 15% loss of YAK3 activity relative to controls without DMSO. Reactions were incubated for 2 hours at room temperature and were stopped by a 75 ul addition of 0.19 μg Streptavidin Scintillation Proximity beads (Amersham Pharmacia Biotech, Catalog No. RPNQ 0007) in PBS, pH 7.4, 10 mM EDTA, 0.1% Triton X-100, 1 mM ATP. Under the assay conditions defined above, the $K_m$(apparent) for ATP was determined to be 7.2±2.4 μM.

TABLE 1

| Example No. compounds | $pIC_{50}$ values |
|---|---|
| 18 | ++++ |
| 98 | ++++ |
| 58 | +++ |
| 13 | ++ |
| 64 | + |

Legend

| $pIC_{50}$ values | Symbol |
|---|---|
| 10-9 | ++++ |
| 8.99-8 | +++ |

-continued

| pIC$_{50}$ values | Symbol |
|---|---|
| 7.99-7 | ++ |
| 6.99-6 | + | pIC$_{50}$ = −log$_{10}$(IC$_{50}$)

Utility of the Present Invention

The above biological data clearly shows that the compounds of formula I or II are useful for treating or preventing disease states in which hYAK3 proteins are implicated, especially diseases of the erythroid and hematopoietic systems, including but not limited to, anemias due to renal insufficiency or to chronic disease, such as autoimmunity, HIV, or cancer, and drug-induced anemias, myelodysplastic syndrome, aplastic anemia, myelosuppression, and cytopenia.

The compounds of formula I or II are especially useful in treating diseases of the hematopoietic system, particularly anemias. Such anemias include an anemia selected from the group comprising: aplastic anemia and myelodysplastic syndrome. Such anemias also include those wherein the anemia is a consequence of a primary disease selected from the group consisting of: cancer, leukemia and lymphoma. Such anemias also include those wherein the anemia is a consequence of a primary disease selected from the group consisting of: renal disease, failure or damage. Such anemias include those wherein the anemia is a consequence of chemotherapy or radiation therapy, in particular wherein the chemotherapy is chemotherapy for cancer or AZT treatment for HIV infection. Such anemias include those wherein the anemia is a consequence of a bone marrow transplant or a stem cell transplant. Such anemias also include anemia of newborn infants, Such anemias also include those which are a consequence of viral, fungal, microbial or parasitic infection.

The compounds of formula I or II are also useful for enhancing normal red blood cell numbers. Such enhancement is desirable for a variety of purposes, especially medical purposes such as preparation of a patient for transfusion and preparation of a patient for surgery.

What is claimed is:

1. A compound of the formula II, or a salt thereof,

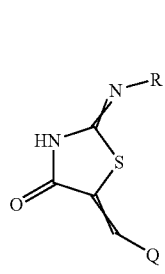

in which
R is $C_{3-6}$ cycloalkyl or naphthyl; or
R is

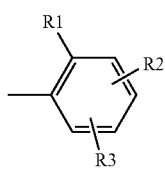

in which R1 is hydrogen, halogen, —$C_{1-6}$alkyl, —$SC_{1-6}$alkyl, —$OC_{1-6}$alkyl, —$NO_2$, —S(=O)—$C_{1-6}$alkyl, —OH, —$CF_3$, —CN, —$CO_2$H, —$OCF_3$, or —$CO_2C_{1-6}$alkyl;
and R2 and R3 are independently hydrogen, halogen, —$C_{1-6}$ alkyl, —$SC_{1-6}$alkyl, —$CO_{1-6}$alkyl, —$NO_2$, —S(=O)—$C_{1-6}$ alkyl, —OH, —$CF_3$, —CN, —$CO_2$H, —$CO_2C_{1-6}$alkyl, —$CONH_2$, —$NH_2$, —$OCH_2$(C=O)OH, —$OCH_2CH_2OCH_3$, —$SO_2NH_2$, —$CH_2SO_2CH_3$, —NH(C=NH)$CH_3$; or R2 and R3 can independently be a radical of the formula

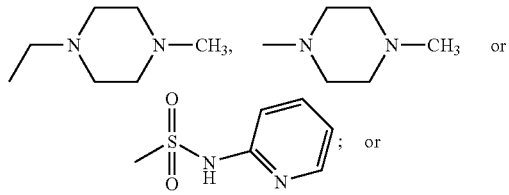

R is

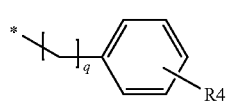

in which q is one or two; R4 is hydrogen, halogen, or —$SO_2NH_2$; or
R is $(CH_2)$—$NR^kR^l$ in which n is 2 or 3, and $R^k$ and $R^l$ are independently —$C_{1-6}$alkyl; or —$NR^kR^l$ together form

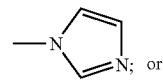

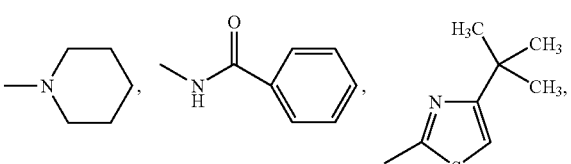

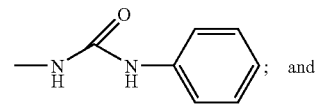

R is
Q is

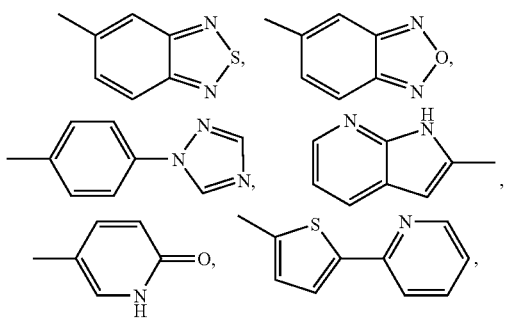

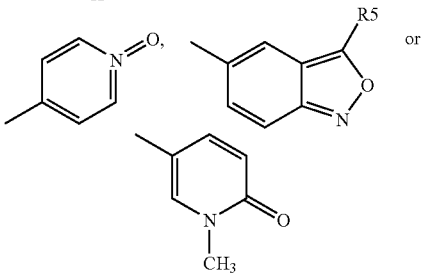

in which R5 is hydrogen, phenyl optionally substituted with up to three $C_{1-6}$ alkyl or halogen, or $C_{1-6}$alkyl; or
Q is

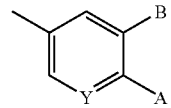

in which Y is CH; and A and B together are a part of

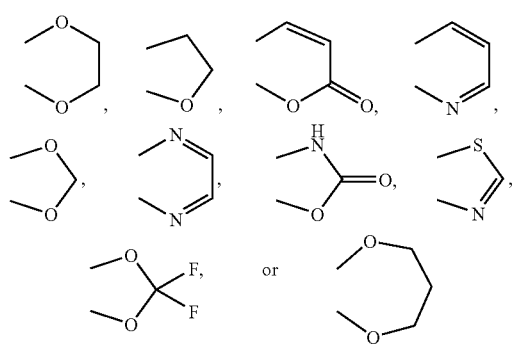

provided that ortho position to Y is N or O.

2. A compound of formula II as described in claim 1 in which

R is $C_{3-6}$ cycloalkyl or naphthyl; or

R is

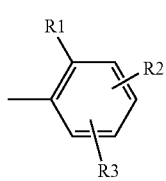

in which R1 is hydrogen, halogen, —$C_{1-6}$alkyl, —$SC_{1-6}$alkyl, —$OC_{1-6}$alkyl, —$NO_2$, —S(=O)—$C_{1-6}$alkyl, —OH, —$CF_3$, —CN, —$CO_2H$, —$OCF_3$, or —$CO_2C_{1-6}$alkyl;

and R2 and R3 are independently hydrogen, halogen, —$C_{1-6}$alkyl, —$SC_{1-6}$alkyl, —$OC_{1-6}$alkyl, —$NO_2$, —S(=O)—$C_{1-6}$alkyl, —OH, —$CF_3$, —CN, —$CO_2H$, —$CO_2C_{1-6}$alkyl, —$CONH_2$, —$NH_2$, —$OCH_2(C=O)$OH, —$OCH_2CH_2OCH_3$, —$SO_2NH_2$, —$CH_2SO_2CH_3$, —NH(C=NH)$CH_3$; or R2 and R3 can independently be a radical of the formula

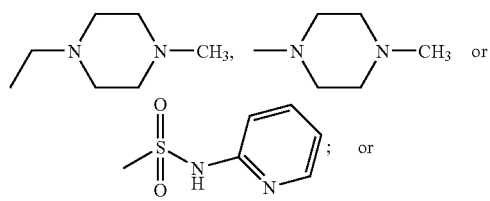

R is

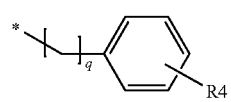

in which q is one or two; R4 is hydrogen, halogen, or —$SO_2NH_2$; or

R is $(CH_2)_n$—$NR^kR^l$ in which n is 2 or 3, and $R^k$ and $R^l$ are independently —$C_{1-6}$alkyl; or $NR^kR^l$ together form

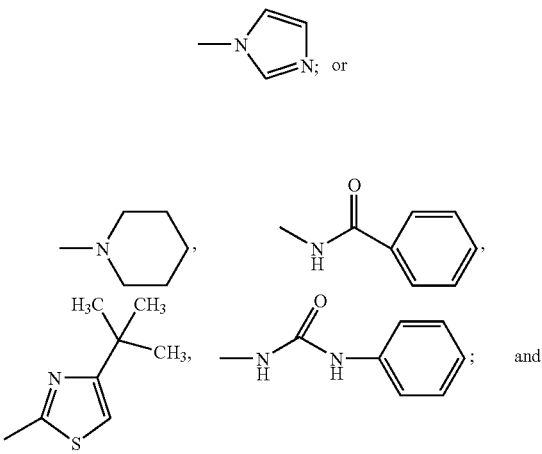

R is

Q is

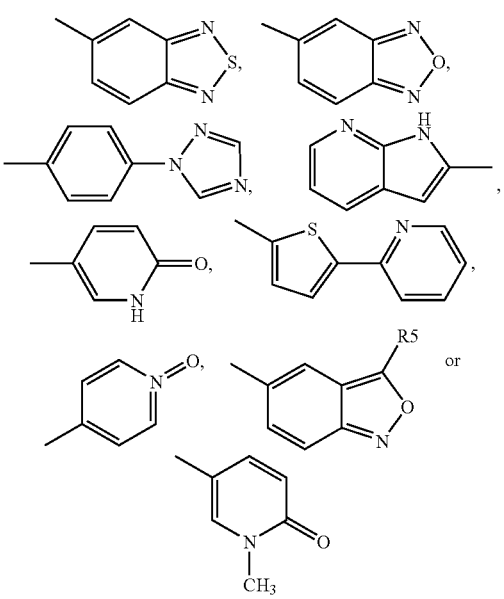

in which R5 is hydrogen, phenyl optionally substituted with up to three $C_{1-6}$ alkyl or halogen, or $C_{1-6}$ alkyl; or Q is

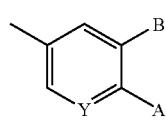

in which Y is CH; and A and B together are a part of

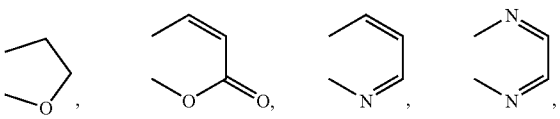

-continued

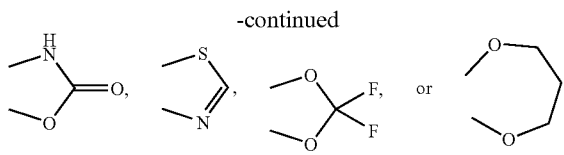

provided that ortho position to Y is N or O, or a salt thereof.

3. A compound of formula II as described in claim 2 in which R is

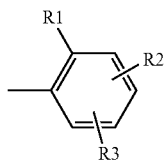

in which R1 is halogen, —C$_{1-6}$alkyl, —SC$_{1-6}$alkyl, —OC$_{1-6}$ alkyl, —NO$_2$, —S(=O)—C$_{1-6}$alkyl, —OH, —CF$_3$, —CN, —CO$_2$H, or —CO$_2$C$_{1-6}$alkyl;

and R2 and R3 are independently hydrogen, halogen, —C$_{1-6}$alkyl, —SC$_{1-6}$alkyl, —OC$_{1-6}$alkyl, —NO$_2$, —S(=O)—C$_{1-6}$alkyl, —OH, —CF$_3$, —CN, —CO$_2$H, —CO$_2$C$_{1-6}$alkyl, —NH$_2$, or —NH(C=NH)CH$_3$;

and

Q is

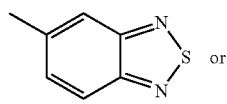

Q is

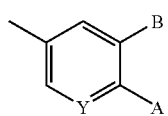

in which Y is CH; and A and B together are a part of

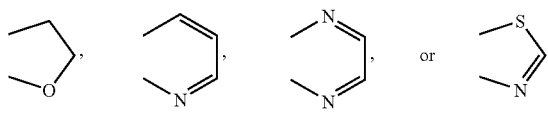

provided that ortho position to Y is N or O, or a salt thereof.

4. A compound of formula II as described in claim 3 in which R is

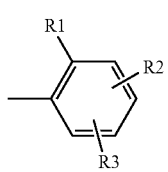

in which R1 is halogen, —C$_{1-6}$alkyl, —SC$_{1-6}$alkyl, —OC$_{1-6}$ alkyl, —NO$_2$, —S(=O)—C$_{1-6}$alkyl, —OH, —CF$_3$, —CN, —CO$_2$H, or —CO$_2$C$_{1-6}$alkyl;

and R2 and R3 are independently hydrogen, halogen, —C$_{1-6}$ alkyl, —SC$_{1-6}$alkyl, —OC$_{1-6}$alkyl, —NO$_2$, —S(=O)—C$_{1-6}$alkyl, —OH, —CF$_3$, —CN, —CO$_2$H, —CO$_2$C$_{1-6}$alkyl, —NH$_2$, or —NH(C=NH)CH$_3$;

and

Q is

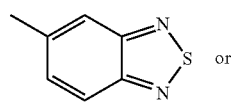

or

Q is

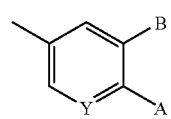

in which Y is CH; and A and B together are a part of

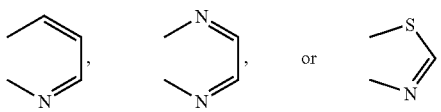

provided that ortho position to Y is N or O, or a salt thereof.

5. A pharmaceutical composition comprising a therapeutically effective amount of a compound of claim 1 or a salt thereof and one or more of pharmaceutically acceptable carriers, diluents and excipients.

6. A compound of claim 1 selected from the group consisting of:
2-(2-Chloro-5-fluoro-phenylimino)-5-(2,3-dihydro-benzo[1-6]dioxin-6-ylmethylene)-thiazolidin-4-one;
2-(2-Chloro-phenylimino)-5-(2-oxo-2H-chromen-6-ylmethylene)-thiazolidin-4-one;
2-(2-Chloro-phenylimino)-5-(2-oxo-2H-chromen-6-ylmethylene)-thiazolidin-4-one;
2-(2-Chloro-phenylimino)-5-(2-oxo-2H-chromen-6-ylmethylene)-thiazolidin-4-one;
5-(2,3-Dihydro-benzofuran-5-ylmethylene)-2-(2,4,6-trimethyl-phenylimino)-thiazolidin-4-one;
2-Cyclohexylimino-5-(2,3-dihydro-benzo[1-6]dioxin-6-ylmethylene)-thiazolidin-4-one;
2-Cyclohexylimino-5-(2,3-dihydro-benzofuran-5-ylmethylene)-thiazolidin-4-one;
5-(2,3-Dihydro-benzofuran-5-ylmethylene)-2-o-totylimino-thiazolidin-4-one;
5-(2,3-Dihydro-benzo[1-6]dioxin-6-ylmethylene)-2-o-tolylimino-thiazolidin-4-one;
5-[2-(2-Chloro-phenylimino)-4-oxo-thiazolidin-5-ylidenemethyl]-3H-benzooxazol-2-one;
2-(2-Trifluoromethyl-phenylimino)-5-(2,3-dihydro-benzofuran-5-ylmethylene)-thiazolidin-4-one;
2-(2-Bromo-phenylimino)-5-(2,3-dihydro-benzofuran-5-ylmethylene)-thiazolidin-4-one;
2-(2,6-Dichloro-phenylimino)-5-(2,3-dihydro-benzofuran-5-ylmethylene)-thiazolidin-4-one;

5-(2,3-Dihydro-benzofuran-5-ylmethylene)-2-(2-methyl-sulfanyl-phenylimino)-thiazolidin-4-one;
5-(2,3-Dihydro-benzofuran-5-ylmethylene)-2-(2-fluoro-phenylimino)-thiazolidin-4-one;
2-(2-Methylsulfanyl-phenylimino)-5-(quinolin-6-ylmethylene)-thiazolidin-4-one;
2-(2-Bromo-phenylimino)-5-(quinolin-6-ylmethylene)-thiazolidin-4-one;
2-(2,3-Dimethyl-phenylimino)-5-(quinolin-6-ylmethylene)-thiazolidin-4-one;
2-(Naphthalen-1-ylimino)-5-(quinolin-6-ylmethylene)-thiazolidin-4-one;
5-(Quinolin-6-ylmethylene)-2-(2-trifluoromethyl-phenylimino)-thiazolidin-4-one;
2-(2-Chloro-5-trifluoromethyl-phenylimino)-5-(quinolin-6-ylmethylene)-thiazolidin-4-one;
2-(2,6-Dichloro-phenylimino)-5-8quinolin-6-ylmethylene)-thiazolidin-4-one;
2-(2-Bromo-phenylimino)-5-(2,3-dihydro-benzo[1-6]dioxin-6-ylmethylene)-thiazolidin-4-one;
2-(2-Chloro-phenylimino)-5-(quinoxalin-6-ylmethylene)-thiazolidin-4-one;
2-(2,6-Dichloro-phenylimino)-5-(2,3-dihydro-benzo[1-6]dioxin-6-ylmethylene)-thiazolidin-4-one;
5-(2,3-Dihydro-benzo[1-6]dioxin-6-ylmethylene)-2-(2-nitro-phenylimino)-thiazolidin-4-one;
5-(2,3-Dihydro-benzofuran-5-ylmethylene)-2-(2-nitro-phenylimino)-thiazolidin-4-one;
2-(2-Chloro-4-fluoro-5-methyl-phenylimino)-5-(2,3-dihydro-benzofuran-5-ylmethylene)-thiazolidin-4-one;
3-Chloro-4-[5-(2,3-dihydro-benzofuran-5-ylmethylene)-4-oxo-thiazolidin-2-ylideneamino]-benzoic acid methyl ester;
2-(2-Chloro-5-fluoro-phenylimino)-5-(2,3-dihydro-benzofuran-5-ylmethylene)-thiazolidin-4-one;
2-(2-Chloro-4-trifluoromethyl-phenylimino)-5-(2,3-dihydro-benzofuran-5-ylmethylene)-thiazolidin-4-one;
2-(4-Bromo-2-chloro-phenylimino)-5-(2,3-dihydro-benzofuran-5-ylmethylene)-thiazolidin-4-one;
5-(2,3-Dihydro-benzofuran-5-ylmethylene)-2-(2-methanesulfinyl-phenylimino)-thiazolidin-4-one;
3-Chloro-4-[5-(2,3-dihydro-benzofuran-5-ylmethylene)-4-oxo-thiazolidin-2-ylideneamino]-benzoic acid;
5-[2-(2-Chloro-phenylimino)-4-oxo-thiazolidin-5-ylidenemethyl]-1H-pyridin-2-one;
2-(2-Methylsulfanyl-phenylimino)-5-(quinolin-6-ylmethylene)-thiazolidin-4-one;
2-(2-Chloro-4-fluoro-5-methyl-phenylimino)-5-(quinolin-6-ylmethylene)-thiazolidin-4-one;
2-(2-Chloro-5-fluoro-phenylimino)-5-(quinolin-6-ylmethylene)-thiazolidin-4-one;
2-(2-Chloro-5-fluoro-phenylimino)-5-(2,3-dihydro-benzo[1-6]dioxin-6-ylmethylene)-thiazolidin-4-one;
2-(2-Chloro-4-trifluoromethyl-phenylimino)-5-quinolin-6-ylmethylene-thiazolidin-4-one;
5-(Benzothiazol-6-ylmethylene)-2-(2-chloro-phenylimino)-thiazolidin-4-one;
5-(Benzo[1,2,5]thiadiazol-5-ylmethylene)-2-(2-bromo-phenylimino)-thiazolidin-4-one;
5-(Benzo[1,2,5]thiadiazol-5-ylmethylene)-2-(2-chloro-5-fluoro-phenylimino)-thiazolidin-4-one;
5-(Benzothiazol-6-ylmethylene)-2-(2,6-dichloro-phenylimino)-thiazolidin-4-one;
2-(2-Chloro-phenylimino)-5-(4-hydroxy-3-nitro-benzylidene)-thiazolidin-4-one;
2-(2-Chloro-phenylimino)-5-(4-hydroxy-3-methoxy-benzylidene)-thiazolidin-4-one;
2-(2-Chloro-phenylimino)-5-(4-hydroxy-benzylidene)-thiazolidin-4-one;
2-(2-Chloro-phenylimino)-5-(4-methoxy-benzylidene)-thiazolidin-4-one;
5-(3-Chloro-4-hydroxy-benzylidene)-2-(2-chloro-phenylimino)-thiazolidin-4-one;
2-(2-Chloro-phenylimino)-5-(3-fluoro-4-methoxy-benzylidene)-thiazolidin-4-one;
2-(2,6-Dichloro-phenylimino)-5-(3-fluoro-4-hydroxy-benzylidene)-thiazolidin-4-one;
2-(2-Chloro-phenylimino)-5-(3-fluoro-4-hydroxy-benzylidene)-thiazolidin-4-one;
2-(2-Chloro-5-fluoro-phenylimino)-5-(3-fluoro-4-hydroxy-benzylidene)-thiazolidin-4-one;
5-(3-Fluoro-4-hydroxy-benzylidene)-2-o-tolylimino-thiazolidin-4-one;
2-(2-Chloro-phenylimino)-5-quinolin-6-ylmethylene-thiazolidin-4-one;
5-Quinolin-6-ylmethylene-2-(2,4,6-trimethyl-phenylimino)-thiazolidin-4-one;
5-Quinolin-6-ylmethylene-2-o-tolylimino-thiazolidin-4-one;
2-(2-Methoxy-phenylimino)-5-quinolin-6-ylmethylene-thiazolidin-4-one;
5-(213-Dihydro-benzofuran-5-ylmethylene)-2-(2-dimethylamino-ethylamino)-thiazol-4-one;
Benzoic acid N'-(4-oxo-5-quinolin-6-ylmethylene-4,5-dihydro-thiazol-2-yl)-hydrazide;
2-(2-Dimethylamino-ethylimino)-5-quinolin-6-ylmethylene-thiazolidin-4-one;
5-(2,3-Dihydro-benzofuran-5-ylmethylene)-2-(piperidin-1-ylamino)-thiazol-4-one;
2-Benzylamino-5-(2,3-dihydro-benzofuran-5-ylmethylene)-thiazol-4-one;
2-(4-tert-Butyl-thiazol-2-ylamino)-5-(2,3-dihydro-benzofuran-5-ylmethylene)-thiazol-4-one;
4-{[5-(2,3-Dihydro-benzofuran-5-ylmethylene)-4-oxo-4,5-dihydro-thiazol-2-ylamino]-methyl}-benzenesulfonamide;
5-(2,3-Dihydro-benzofuran-5-ylmethylene)-2-(3-dimethylamino-propylamino)-thiazol-4-one;
5-(23-Dihydro-benzofuran-5-ylmethylene)-2-(3-imidazol-1-yl-propylamino)-thiazol-4-one;
Phenyl-carbamic acid N'-[5-(2,3-dihydro-benzofuran-5-ylmethylene)-4-oxo-4,5-dihydro-thiazol-2-yl]-hydrazide;
Benzoic acid N'-[5-(2,3-dihydro-benzofuran-5-ylmethylene)-4-oxo-4,5-dihydro-thiazol-2-yl]-hydrazide;
5-Benzo[1,2,5]thiadiazol-5-ylmethylene-2-(2,3,4-trifluoro-phenylamino)-thiazol-4-one;
5-Benzo[1,2,5]oxadiazol-5-ylmethylene-2-(2-nitro-phenylamino)-thiazol-4-one;
2-(2,6-Dichloro-phenylamino)-5-(4-[1,2,4]triazol-1-yl-benzylidene)-thiazol-4-one;
2-(2,6-Dichloro-phenylamino)-5-(1H-pyrrolo[2,3-b]pyridin-2-ylmethylene)-thiazol-4-one;
5-Benzo[1,2,5]thiadiazol-5-ylmethylene-2-(2,6-dichloro-phenylamino)-thiazol-4-one;
5-[2-(2-Methoxy-6-methyl-phenylamino)-4-oxo-4H-thiazol-5-ylidenemethyl]-1H-pyridin-2-one;
5-Benzo[1,2,5]thiadiazol-5-ylmethylene-2-(2-nitro-phenylamino)-thiazol-4-one;
2-(2-Bromo-6-fluoro-phenylamino)-5-quinolin-6-ylmethylene-thiazol-4-one;
2-(2-Methoxy-6-methyl-phenylamino)-5-quinolin-6-ylmethylene-thiazol-4-one;

5-Quinolin-6-ylmethylene-2-(2,3,4-trifluoro-phenylamino)-thiazol-4-one;

2-(2,6-Dichloro-phenylamino)-5-(2-oxo-2H-chromen-6-ylmethylene)-thiazol-4-one;

2-(2-Bromo-phenylamino)-5-(5-pyridin-2-yl-thiophen-2-ylmethylene)-thiazol-4-one;

2-(2-Bromo-phenylamino)-5-(1-oxy-pyridin-4-ylmethylene)-thiazol-4-one;

2-(2-Bromo-phenylamino)-5-(3-p-tolyl-benzo[c]isoxazol-5-ylmethylene)-thiazol-4-one;

2-(2-Bromo-phenylamino)-5-(3,4-dihydro-2H-benzo[b][1-6]dioxepin-7-ylmethylene)-thiazol-4-one;

5-Benzo[1,2,5]oxadiazol-5-ylmethylene-2-(2-bromo-phenylamino)-thiazol-4-one;

2-(2,6-Dichloro-phenylamino)-5-(2-methoxy-pyridin-3-ylmethylene)-thiazol-4-one;

2-(2-Chloro-phenylamino)-5-(6-methoxy-pyridin-3-ylmethylene)-thiazol-4-one;

2-(2-Chloro-5-trifluoromethyl-phenylamino)-5-quinolin-6-ylmethylene-thiazol-4-one;

2-(2-Bromo-phenylamino)-5-(4-hydroxy-3-methoxy-benzylidene)-thiazol-4-one;

5-(2,3-Dihydro-benzofuran-5-ylmethylene)-2-(2-methoxy-phenylamino)-thiazol-4-one;

2-(2-Nitro-phenylamino)-5-quinolin-6-ylmethylene-thiazol-4-one 2-(2-Bromo-phenylamino)-5-(3,4-diamino-benzylidene)-thiazol-4-one;

5-[2-(2-Chloro-phenylimino)-4-oxo-thiazolidin-5-ylidenemethyl]-1-methyl-1H-pyridin-2-one;

2-(2-Chloro-5-nitro-phenylamino)-5-quinolin-6-ylmethylene-thiazol-4-one;

2-(5-Amino-2-chloro-phenylamino)-5-quinolin-6-ylmethylene-thiazol-4-one;

N-[4-Chloro-3-(4-oxo-5-quinolin-6-ylmethylene-4,5-dihydro-thiazol-2-ylamino)-phenyl]-acetamidine hydrochloride;

4-{[4-oxo-5-(6-quinolinylmethylidene)-4,5-dihydro-1,3-thiazol-2-yl]amino}benzamide;

3-{[4-oxo-5-(6-quinolinylmethylidene)-4,5-dihydro-1,3-thiazol-2-yl]amino}benzenesulfonamide;

4-{[4-oxo-5-(6-quinolinylmethylidene)-4,5-dihydro-1,3-thiazol-2-yl]amino}-N-2-pyridinylbenzenesulfonamide;

2-({4-[(4-methyl-1-piperazinyl)methyl]phenyl}amino)-5-(6-quinolinylmethylidene)-1,3-thiazol-4(5H)-one;

2-({4-[(methylsulfonyl)methyl]phenyl}amino)-5-(6-quinolinylmethylidene)-1,3-thiazol-4(5H)-one;

2-({3-[(methylsulfonyl)methyl]phenyl}amino)-5-(6-quinolinylmethylidene)-1,3-thiazol-4(5H)-one;

2-{[4-(4-methyl-1-piperazinyl)phenyl]amino}5-(6-quinolinylmethylidene)-1,3-thiazol-4(5H)-one;

2-{[2-(3-chlorophenyl)ethyl]amino}-5-(6-quinolinylmethylidene)-1,3-thiazol-4(5H)-one;

4-(2-{[4-oxo-5-(6-quinolinylmethylidene)-4,5-dihydro-1,3-thiazol-2-yl]amino}ethyl)benzenesulfonamide;

3-{[4-oxo-5-(6-quinolinylmethylidene)-4,5-dihydro-1,3-thiazol-2-yl]amino}benzamide;

2-[(2,6-Difluoro-phenylamino)-methylene]-5-quinolin-6-ylmethylene-thiazolidin-4-one;

2-[(2,6-Difluoro-phenylamino)-methylene]-5-quinolin-6-ylmethylene-thiazolidin-4-one;

[2,4-Dichloro-5-(4-oxo-5-quinolin-6-ylmethylene-thiazolidin-2-ylideneamino)-phenoxy]-acetic acid;

2-[2,4-Dichloro-5-(2-methoxy-ethoxy)-phenylimino]-5-quinolin-6-ylmethylene-thiazolidin-4-one;

4-Chloro-3-(4-oxo-5-quinolin-6-ylmethylene-thiazolidin-2-ylideneamino)-benzoic acid; and

[2,4-Dichloro-5-(4-oxo-5-quinolin-6-ylmethylene-thiazolidin-2-ylideneamino)-phenoxy]-acetic acid, or a salt thereof.

* * * * *

SEQUENCE LISTING

<160> NUMBER OF SEQ ID NOS: 2

<210> SEQ ID NO 1
<211> LENGTH: 16
<212> TYPE: PRT
<213> ORGANISM: bovine

<400> SEQUENCE: 1

Leu Gly Gly Arg Asp Ser Arg Ala Gly Ser Pro Met Ala Arg Arg His
 1               5                   10                  15

<210> SEQ ID NO 2
<211> LENGTH: 588
<212> TYPE: PRT
<213> ORGANISM: human

<400> SEQUENCE: 2

Met Gly Gly Thr Ala Arg Gly Pro Gly Arg Lys Asp Ala Gly Pro Pro
 1               5                   10                  15

Gly Ala Gly Leu Pro Pro Gln Gln Arg Arg Leu Gly Asp Gly Val Tyr
                20                  25                  30

Asp Thr Phe Met Met Ile Asp Glu Thr Lys Cys Pro Pro Cys Ser Asn
                35                  40                  45

Val Leu Cys Asn Pro Ser Glu Pro Pro Pro Arg Arg Leu Asn Met
     50                  55                  60

Thr Thr Glu Gln Phe Thr Gly Asp His Thr Gln His Phe Leu Asp Gly
 65                  70                  75                  80

Gly Glu Met Lys Val Glu Gln Leu Phe Gln Glu Phe Gly Asn Arg Lys
                85                  90                  95

Ser Asn Thr Ile Gln Ser Asp Gly Ile Ser Asp Ser Glu Lys Cys Ser
                100                 105                 110

Pro Thr Val Ser Gln Gly Lys Ser Ser Asp Cys Leu Asn Thr Val Lys
            115                 120                 125

Ser Asn Ser Ser Ser Lys Ala Pro Lys Val Val Pro Leu Thr Pro Glu
        130                 135                 140

Gln Ala Leu Lys Gln Tyr Lys His His Leu Thr Ala Tyr Glu Lys Leu
145                 150                 155                 160

```
Glu Ile Ile Asn Tyr Pro Glu Ile Tyr Phe Val Gly Pro Asn Ala Lys
                165                 170                 175
Lys Arg His Gly Val Ile Gly Pro Asn Asn Gly Gly Tyr Asp Asp
                180                 185                 190
Ala Asp Gly Ala Tyr Ile His Val Pro Arg Asp His Leu Ala Tyr Arg
            195                 200                 205
Tyr Glu Val Leu Lys Ile Ile Gly Lys Gly Ser Phe Gly Gln Val Ala
        210                 215                 220
Arg Val Tyr Asp His Lys Leu Arg Gln Tyr Val Ala Leu Lys Met Val
225                 230                 235                 240
Arg Asn Glu Lys Arg Phe His Arg Gln Ala Ala Glu Ile Arg Ile
                245                 250                 255
Leu Glu His Leu Lys Lys Gln Asp Lys Thr Gly Ser Met Asn Val Ile
                260                 265                 270
His Met Leu Glu Ser Phe Thr Phe Arg Asn His Val Cys Met Ala Phe
            275                 280                 285
Glu Leu Leu Ser Ile Asp Leu Tyr Glu Leu Ile Lys Lys Asn Lys Phe
        290                 295                 300
Gln Gly Phe Ser Val Gln Leu Val Arg Lys Phe Ala Gln Ser Ile Leu
305                 310                 315                 320
Gln Ser Leu Asp Ala Leu His Lys Asn Lys Ile Ile His Cys Asp Leu
                325                 330                 335
Lys Pro Glu Asn Ile Leu Leu Lys His His Gly Arg Ser Ser Thr Lys
                340                 345                 350
Val Ile Asp Phe Gly Ser Ser Cys Phe Glu Tyr Gln Lys Leu Tyr Thr
            355                 360                 365
Tyr Ile Gln Ser Arg Phe Tyr Arg Ala Pro Glu Ile Ile Leu Gly Ser
        370                 375                 380
Arg Tyr Ser Thr Pro Ile Asp Ile Trp Ser Phe Gly Cys Ile Leu Ala
385                 390                 395                 400
Glu Leu Leu Thr Gly Gln Pro Leu Phe Pro Gly Glu Asp Glu Gly Asp
                405                 410                 415
Gln Leu Ala Cys Met Met Glu Leu Leu Gly Met Pro Pro Lys Leu
            420                 425                 430
Leu Glu Gln Ser Lys Arg Ala Lys Tyr Phe Ile Asn Ser Lys Gly Ile
        435                 440                 445
Pro Arg Tyr Cys Ser Val Thr Thr Gln Ala Asp Gly Arg Val Val Leu
        450                 455                 460
Val Gly Gly Arg Ser Arg Arg Gly Lys Lys Arg Gly Pro Pro Gly Ser
465                 470                 475                 480
Lys Asp Trp Gly Thr Ala Leu Lys Gly Cys Asp Asp Tyr Leu Phe Ile
                485                 490                 495
Glu Phe Leu Lys Arg Cys Leu His Trp Asp Pro Ser Ala Arg Leu Thr
                500                 505                 510
Pro Ala Gln Ala Leu Arg His Pro Trp Ile Ser Lys Ser Val Pro Arg
            515                 520                 525
Pro Leu Thr Thr Ile Asp Lys Val Ser Gly Lys Arg Val Val Asn Pro
        530                 535                 540
Ala Ser Ala Phe Gln Gly Leu Gly Ser Lys Leu Pro Pro Val Val Gly
545                 550                 555                 560
Ile Ala Asn Lys Leu Lys Ala Asn Leu Met Ser Glu Thr Asn Gly Ser
                565                 570                 575
```

```
Ile Pro Leu Cys Ser Val Leu Pro Lys Leu Ile Ser
            580             585
```